US012577312B2

(12) United States Patent
Moschos et al.

(10) Patent No.: US 12,577,312 B2
(45) Date of Patent: Mar. 17, 2026

(54) METHODS FOR THE TREATMENT OF MELANOMA USING COMPOSITIONS OF DENOSUMAB AND PD-1 INHIBITOR

(71) Applicant: The University of North Carolina at Chapel Hill, Chapel Hill, NC (US)

(72) Inventors: Stergios Moschos, Chapel Hill, NC (US); Maureen Su, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 19/064,136

(22) Filed: Feb. 26, 2025

(65) Prior Publication Data

US 2025/0188178 A1 Jun. 12, 2025

Related U.S. Application Data

(63) Continuation of application No. PCT/US2023/074871, filed on Sep. 22, 2023.

(60) Provisional application No. 63/409,348, filed on Sep. 23, 2022.

(51) Int. Cl.
| | |
|---|---|
| *A61K 39/395* | (2006.01) |
| *A61P 35/00* | (2006.01) |
| *C07K 16/28* | (2006.01) |
| *A61K 39/00* | (2006.01) |

(52) U.S. Cl.
CPC .......... *C07K 16/2875* (2013.01); *A61P 35/00* (2018.01); *C07K 16/2818* (2013.01); *A61K 2039/507* (2013.01); *A61K 2039/545* (2013.01)

(58) Field of Classification Search
None
See application file for complete search history.

(56) References Cited

U.S. PATENT DOCUMENTS

| | | |
|---|---|---|
| 7,364,736 B2 | 4/2008 | Boyle et al. |
| 2023/0042913 A1 | 2/2023 | Dougall et al. |

FOREIGN PATENT DOCUMENTS

WO WO-2019080909 A1 5/2019

OTHER PUBLICATIONS

NIH Inxight Drugs Database, Nivolumab 31YO63LBSN, Retrieved online from :<URL:https://drugs.ncats.io/drug/31YO63LBSN>, [retrieved on Apr. 21, 2025], 2025.*
NIH Inxight Drugs Database, Pembrolizumab DPT0O3T46PRetrieved online from :<URL:https://drugs.ncats.io/drug/DPT0O3T46P>, [retrieved on Apr. 21, 2025], 2025.*

NIH Inxight Drugs Database, Denosumab 4EQZ6YO2HI, Retrieved online from :<URL:https://drugs.ncats.io/drug/denosumab>, [retrieved on Apr. 21, 2025], 2025.*
ClinicalTrials.gov Database, NCT03620019, Denosumab + PD-1 in Subjects With Stage III/ IV Melanoma, ver.5, Retrieved online from: <URL:https://clinicaltrials.gov/study/NCT03620019?term= nct03620019&rank=1&tab=history&a=5#version-content-panel> [retrieved Apr. 21, 2025], Jun. 24, 2019.*
Pitiot et al.. Alternative Routes of Administration for Therapeutic Antibodies-State of the Art, Antibodies, 11(3):56, 25 pages, doi: 10.3390/antib11030056, Aug. 22, 2022.*
ClinicalTrial.gov Database, NCT01866319 (Keynote-006), Retrieved online from: <URL: https://clinicaltrials.gov/study/NCT01866319> [retrieved on Apr. 22, 2025], Jun. 2, 2020.*
ClinicalTrial.gov Database, NCT03151756 (CHARLI), ver. 12, Retrieved online from: <URLhttps://clinicaltrials.gov/study/ NCT03161756?cond=Melanoma&intr=denosumab,%20AMG-162,% 20prolia,%20xgeva,%20AMg162&viewType=Card&rank=1&tab= history&a=12#version-content-panel, [retrieved on Apr. 21, 2025] Mar. 21, 2021.*
Tawbi et al., Relatlimab and Nivolumab versus Nivolumab in Untreated Advanced Melanoma, N. Engl. J. Med.; 386:24-34, 2022.*
Damsky et al., Decoding melanoma metastasis, Cancers, 3121-163, 2011.*
ClincialTrials.gov Database, NCT03620019, Denosumab + PD-1 in Subjects With Stage III/ IV Melanoma, ver. 9, Retrieved online from: <URL:https://clinicaltrials.gov/study/NCT03620019?term= NCT03620019&rank=1&tab=history&a=9#version-content-panel> [retrieved on Nov. 21, 2025], Jul. 20, 2022.*
ClincialTrials.gov Database, NCT03161756, Evaluation of Denosumab in Combination With Immune Checkpoint Inhibitors in Patients With Unresectable or Metastatic Melanoma (CHARLI), Retrieved from:<URL:https://clinicaltrials.gov/study/NCT03161756?term= nct03161756&rank=1&tab=table>[retreived on Nov. 21, 2025] Apr. 7, 2022.*
Afzal et al., Immune checkpoint inhibitor (anti-CTLA-4, anti-PD-1) therapy alone versus immune checkpoint inhibitor (anti-CTLA-4, anti-PD-1) therapy in combination with anti-RANKL denosumab in malignant melanoma: a retrospective analysis at a tertiary care center, Melanoma Res., 28(4):341-7 (2018).
Ahern et al., Activator of NFkB ligand (RANKL) inhibition in nonsmall cell lung cancer (NSCLC) (POPCORN), J. Clin. Oncol., supplement 8(37), Abstract, Mar. 2019.
Ahern et al., An observational study of concomitant immunotherapies and denosumab in patients with advanced melanoma or lung cancer, Asia-Pacific Journal of Clinical Oncology, Supplement 3(14):57, Blackwell Publishing Ltd. (Aug. 2018).
Ahern et al., Co-administration of RANKL and CTLA4 Antibodies Enhances Lymphocyte-Mediated Antitumor Immunity in Mice, Clin. Cancer Res., 23(19):5789-801 (2017).

(Continued)

*Primary Examiner* — Claire Kaufman
(74) *Attorney, Agent, or Firm* — MARSHALL, GERSTEIN & BORUN LLP

(57) ABSTRACT

Disclosed herein are methods of treating melanoma, such as, e.g., stage III/IV cutaneous or mucosal melanoma, in a subject in need thereof, comprising administering a therapeutically effective amount of denosumab to the subject and optionally co-administering a therapeutically effective amount of a PD-1 inhibitor to the subject; uses of denosumab or a PD-1 inhibitor in the manufacture of a medicament adapted for use in a method described herein; and pharmaceutical compositions comprising denosumab and/or a PD-1 inhibitor for use in a method described herein.

18 Claims, 1 Drawing Sheet

Specification includes a Sequence Listing.

(56)          References Cited

OTHER PUBLICATIONS

Ahern et al., Pharmacodynamics of Pre-Operative PD1 checkpoint blockade and receptor activator of NFkB ligand (RANKL) inhibition in non-small cell lung cancer (NSCLC): study protocol for a multicentre, open-label, phase 1B/2, translational trial (POPCORN), Trials, 20(1):753 (2019).

Ahern et al., RANKL blockade improves efficacy of PD1-PD-L1 blockade or dual PD1-PD-L1 and CTLA4 blockade in mouse models of cancer, Oncoimmunology, 7(6):e1431088 (2018).

Angela et al., Combination of denosumab and immune checkpoint inhibition: experience in 29 patients with metastatic melanoma and bone metastases, Cancer Immunology, Immunotherapy, 68:1187-94 (2019).

Asano et al., The Therapeutic Effect and Clinical Outcome of Immune Checkpoint Inhibitors on Bone Metastasis in Advanced Non-Small-Cell Lung Cancer, Front Oncol., 12:871675 (2022).

Asano et al., Therapeutic effects and clinical outcomes of immune checkpoint inhibitors on bone metastases in lung cancer, American Society of Clinical Oncology, Abstracts, 321118 (2022).

Bakhru et al., Combination central tolerance and peripheral checkpoint blockade unleashes antimelanoma immunity, JCI Insight, 2(18):e93265 (2017).

Blank et al., Neoadjuvant versus adjuvant ipilimumab plus nivolumab in macroscopic stage III melanoma, Nat. Med., 24(11):1655-61 (2018).

Cancer Genomic Atlas N: Genomic Classification of Cutaneous Melanoma, Cell, 161:1681-96 (2015).

Cao et al., Does denosumab offer survival benefits? Our experience with denosumab in metastatic non-small cell lung cancer patients treated with immune-checkpoint inhibitors, J. Thorac. Dis., 13(8):4668-77 (2021).

Chung et al., Refractory hypercalcemia due to ectopic production of calcitriol in malignant sarcomatoid mesothelioma, Abstract 315, AJKD, 79(4 Suppl2):S96 (Apr. 2022).

Coleman et al., Adjuvant denosumab in early breast cancer (D-CARE): an international, multicentre, randomised, controlled, phase 3 trial, Lancet Oncol., 21(1):60-72 (Jan. 2020).

Decroisette et al., A phase II trial of nivolumab and denosumab association as second-line treatment for stage IV non-small-cell lung cancer (NSCLC) with bone metastases: DENIVOS study (GFPC Jun. 2017), Annals of Oncology, vol. 33, Issue S7, Abstract 1035P (2022).

Denosumab, International Nonproprietary Names for Pharmaceutical Substances (INN), Recommended INN: List 56, WHO Drug Information, vol. 20 No. 3, p. 205-236, (2006).

Dinh et al., Bone and mineral metabolism: Bone and mineral case report, Journal of Endocrine Society, 5(1):A223 (Apr.-May 2021).

Gedye et al., Denosumab and pembrolizumab in clear cell renal carcinoma, Meeting Abstract 2021: Genitourinary cancers symposium, Journal of Clinical Oncology, 39(6):suppl. TPS367, (Mar. 2, 2021).

Gedye et al., Pembrolizumab and denosumab in clear cell renal cell carcinoma (ccRCC): A phase II trial (KeyPAD, ANZUP1601), Annals of Oncology, 34(S2): S1014, 1886P (2023).

Hodi et al., Nivolumab plus ipilimumab or nivolumab alone versus ipilimumab alone in advanced melanoma (CheckMate 067): 4-year outcomes of a multicentre, randomised, phase 3 trial, Lancet Oncol., 19(11):1480-92 (2018).

International Search Report and Written Opinion, International Application No. PCT/US2023/074871, mailed Feb. 12, 2024.

Invitation to Pay Additional Fees and, Where Applicable, Protest Fee, International Application No. PCT/US2023/074871, mailed Dec. 20, 2023.

Johnson et al., Nivolumab in melanoma: latest evidence and clinical potential, Ther Adv Med Oncol., 7(2):97-106 (2015).

Khan et al., Immune checkpoint inhibitor-induced colitis presenting as lymphocytic colitis, Cureus, 13(9):E18085 (Sep. 2021).

Kostenuik et al., Denosumab, a Fully Human Monoclonal Antibody to RANKL, Inhibits Bone Resorption and Increases BMD in Knock-In Mice That Express Chimeric (Murine/Human) RANKL, J. Bone Miner. Res., 24(2):182-95 (2009).

Lau et al., A phase Ib/II trial of ipilimumab-nivolumab-denosumab and nivolumab-denosumab in patients with unresectable stage III and IV melanoma: trial in progress, SMR Congress 2017 abstracts (Dec. 22, 2017).

Li et al., Denosumab in combination with PD-1 checkpoint blockade for MAINtenance therapy of KRAS-mutant advanced NSCLC after first-line immunotherapy: a prospective, single-arm, phase II trial (DEMAIN), Abstract 1409P, Annals of Oncology, vol. 34, Supplement 2, S806 (Oct. 2023).

Liede et al., An observational study of concomitant immunotherapies and denosumab in patients with advanced melanoma or lung cancer, Oncoimmunology, 7(12):e1480301 (2018).

Link et al., Clinical response to re-exposure to high dose MTX in multiply relapsed osteosacrcoma pediatric patients, Pediatric Blood and Cancer, suppl. Supplement 2 66: S123 (Jun. 2019).

Luka et al., Dual immunotherapy for the treatment of metastatic kidney cancer in a patient undergoing hemodialysis, Libri Oncologici, Suppl. Supplement 1 51:10-12 (2023).

Moschos et al., Denosumab improves clinical benefit of PD1 inhibitors in metastatic melanoma (MM) presumably via a suppressive effect on immunoregulatory myeloid cell populations, J. Immunother Cancer, 12(Suppl 3):A1696 (2024).

Myoken et al., Osteonecrosis of the jaw in a metastatic lung cancer patient with bone metastases undergoing pembrolizumab + denosumab combination therapy: Case report and literature review, Oral Oncol., 111:104874 (Dec. 2020).

Ozaki et al., Combined treatment of patients with bone metastases from various cancers with nivolumab plus denosumab: a retrospective study, Journal of Clinical Oncology, Meeting Abstract: 2019 ASCO Annual Meeting 1 (May 26, 2019).

Peters et al., The RANK-RANKL axis: an opportunity for drug repurposing in cancer?, Clin. Transl Oncol., 21(8):977-91 (2019).

Robert et al., Pembrolizumab versus Ipilimumab in Advanced Melanoma, N Engl J Med., 372(26):2521-32 (2015).

Siegel et al., Cancer statistics, 2022, CA Cancer J. Clin., 72(1):7-33 (Jan. 2022).

Smith et al., Denosumab and Bone Metastasis-Free Survival in Men With Nonmetastatic Castration-Resistant Prostate Cancer: Exploratory Analyses by Baseline Prostate-Specific Antigen Doubling Time, J. Clin. Oncol., 31(30):3800-6 (2013).

Sumbly et al., A rare case of pulmonary large cell neuroendocrine carcinoma, Abstract P13, J. Investig. Med., 69:930 (2021).

Tan et al., A phase 1B dose escalation study of ETC-159 in combination with pembrolizumab in advanced or metastatic solid tumours, American Society of Clinical Oncology, Poster Session 2601 (Jun. 2023).

Wang et al., Efficacy and influencing clinical factors of tislelizumab combined with chemotherapy plus bone-targeted agents for NSCLC bone metastasis, Abstract EP.11A.17, Journal of Thoracic Oncology, vol. 19, Issue 10, Supplement, S603 (Oct. 2024).

Wilson et al., Adjuvant nivolumab in high-risk stage IIb/IIc melanoma patients: Results from investigator initiated clinical trial, J. Clin. Oncol., Meetings Abstract: 2021 ASCO Annual Meeting I (May 28, 2021).

Yoshida et al., Successful Treatment of Multiple Metastatic Melanoma with Nivolumab, Ipilimumab plus Denosumab Combined Therapy, Case Rep Oncol., 12(3):829-33 (2019).

Hanley et al., Denosumab: mechanism of action and clinical outcomes, Int J Clin Pract., 66(12):1139-46 (2012).

Gnant et al., Adjuvant denosumab in postmenopausal patients with hormone receptor-positive breast cancer (ABCSG-18): disease-free survival results from a randomised, double-blind, placebo-controlled, phase 3 trial, Lancet Oncol., 20(3):339-51 (2019).

Eisen et al., Use of Adjuvant Bisphosphonates and Other Bone-Modifying Agents in Breast Cancer: ASCO-OH (CCO) Guideline Update, J. Clin. Oncol., 40(7):787-800 (2022).

(56)            References Cited

OTHER PUBLICATIONS

Schaper-Gerhardt et al., The RANKL inhibitor denosumab in combination with dual checkpoint inhibition is associated with increased CXCL-13 serum concentrations, Eur. J. Cancer, 202:113984 (May 2024).

EU Clinical Trials Register, Member state concerned: Germany—PEI, EudraCT No. 2016-001925-15, Title: Effects of a treatment with Denosumab, applied together with either Nivolumab order Pembrolizumab, in patients with skin cancer and bone metastases. Sponsor's protocol code No. ISS20159321 (Aug. 23, 2018).

Huang et al., "T-cell invigoration to tumor burden ratio associated with anti-PD-1 response", Nature, vol. 545, pp. 60-65 (May 2017).

Kupas et al., "RANK is expressed in metastatic melanoma and highly upregulated on melanoma-initiating cells", Journal of Investigative Dermatology, vol. 131, pp. 944-955 (2011).

Lipson et al., "Nivolumab plus relatlimab in advanced melanoma: RELATIVITY-047 4 year update", European Journal of Cancer, 225, pp. 1-8 (2025).

Pilard et al., "RANKL blockade inhibits cancer growth through reversing the tolerogenic profile of tumor-infiltrating (plasmacytoid) dendritic cells", Journal for Immuno Therapy of Cancer, 13:e010753 (2025).

\* cited by examiner

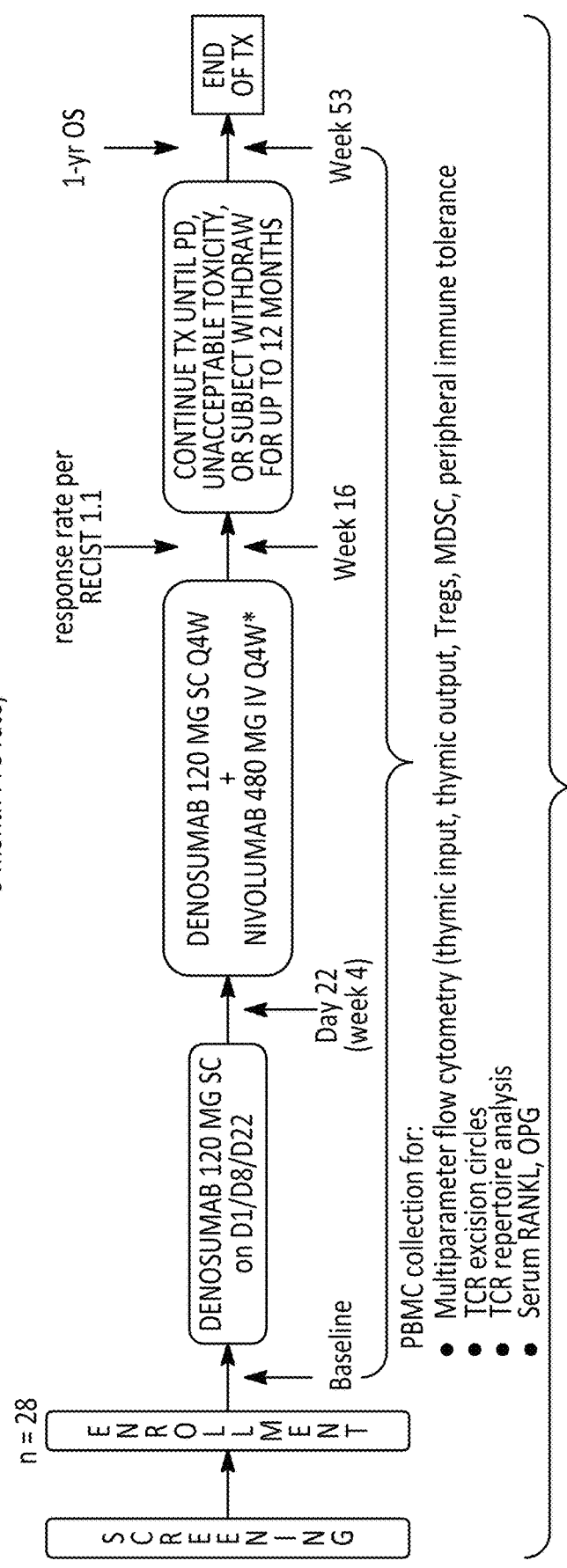

SEQUENCE LISTING

```
Sequence total quantity: 32
SEQ ID NO: 1            moltype = AA  length = 317
FEATURE                 Location/Qualifiers
source                  1..317
                        mol_type = protein
                        organism = Homo sapiens
SEQUENCE: 1
MRRASRDYTK YLRGSEEMGG GPGAPHEGPL HAPPPPAPHQ PPAASRSMFV ALLGLGLGQV   60
VCSVALFFYF RAQMDPNRIS EDGTHCIYRI LRLHENADFQ DTTLESQDTK LIPDSCRRIK  120
QAFQGAVQKE LQHIVGSQHI RAEKAMVDGS WLDLAKRSKL EAQPFAHLTI NATDIPSGSH  180
KVSLSSWYHD RGWAKISNMT FSNGKLIVNQ DGFYYLYANI CFRHHETSGD LATEYLQLMV  240
YVTKTSIKIP SSHTLMKGGS TKYWSGNSEF HFYSINVGGF FKLRSGEEIS IEVSNPSLLD  300
PDQDATYFGA FKVRDID                                                 317

SEQ ID NO: 2            moltype = DNA  length = 2201
FEATURE                 Location/Qualifiers
source                  1..2201
                        mol_type = genomic DNA
                        organism = Homo sapiens
SEQUENCE: 2
gcccgctcgc ccgcgcgccc caggacccaa agccgggctc caagtcggcg ccccacgtcg   60
aggctccgcc gcagcctccg gagttggccg cagacaagaa ggggagggag cgggagaggg  120
aggagagctc cgaagcgaga gggccgagcg ccatgcgccg cgccagcaga gactacacca  180
agtacctgcg tggctcggag gagatgggcg gcgggccccg gagcccgcac gagggccccc  240
tgcacgcccc gccgccgcct gcgccgcacc agccccctgc cgcctcccgc tccatgttcg  300
tggccctcct ggggctgggg ctgggccagg ttgtctgcag cgtcgccctg ttcttctatt  360
tcagagcgca gatggatcct aatagaatat cagaagatgg cactcactgc atttataaa  420
ttttgagact ccatgaaaat gcagattttc aagacacaac tctggagagt caagatacaa  480
aattaatacc tgattcatgt aggagaatta aacaggcctt tcaaggagct gtgcaaaagg  540
aattacaaca tatcgttgga tcacagcaca tcagagcaga gaaagcgatg gtggatggct  600
catggttaga tctggccaag aggagcaagc ttgaagctca gccttttgct catctcacta  660
ttaatgccac cgacatccca tctggttccc ataaagtgag tctgtcctct tggtaccatg  720
atcggggttg ggccaagatc tccaacatga cttttagcaa tggaaaacta atagttaatc  780
```

```
aggatggctt ttattacctg tatgccaaca tttgctttcg acatcatgaa acttcaggag    840
acctagctac agagtatctt caactaatgg tgtacgtcac taaaaccagc atcaaaatcc    900
caagttctca taccctgatg aaaggaggaa gcaccaagta ttggtcaggg aattctgaat    960
tccatttta ttccataaac gttggtggat tttttaagtt acggtctgga gaggaaatca   1020
gcatcgaggt ctccaacccc tccttactgg atccggatca ggatgcaaca tactttgggg   1080
cttttaaagt tcgagatata gattgagccc cagtttttgg agtgttatgt atttcctgga   1140
tgtttggaaa catttttaa aacaagccaa gaaagatgta tataggtgtg tgagactact   1200
aagaggcatg gccccaacgg tacacgactc agtatccatg ctcttgacct tgtagagaac   1260
acgcgtattt acagccagtg ggagatgtta gactcatggt gtgttacaca atggttttta   1320
aatttgtaa tgaattccta gaattaaacc agattggagc aattacgggg tgaccttatg   1380
agaaactgca tgtgggctat gggaggggtt ggtccctggt catgtgcccc ttcgcagctg   1440
aagtggagag ggtgtcatct agcgcaattg aaggatcatc tgaaggggca aattcttttg   1500
aattgttaca tcatgctgga acctgcaaaa aatactttt ctaatgagga gagaaatat   1560
atgtatttt atataatatc taaagttata tttcagatgt aatgttttct ttgcaaagta   1620
ttgtaaatta tatttgtgct atagtatttg attcaaaata tttaaaaatg tcttgctgtt   1680
gacatattta atgtttaaa tgtacagaca tatttaactg gtgcactttg taaattccct   1740
ggggaaaact tgcagctaag gaggggaaaa aaatgttgtt tcctaatatc aaatgcagta   1800
tatttcttcg ttctttttaa gttaatagat tttttcagac ttgtcaagcc tgtgcaaaaa   1860
aattaaaatg gatgccttga ataataagca ggatgttggc caccaggtgc ctttcaaatt   1920
tagaaactaa ttgactttag aaagctgaca ttgccaaaaa ggatacataa tgggccactg   1980
aaatctgtca agagtagtta tataattgtt gaacaggtgt ttttccacaa gtgccgcaaa   2040
ttgtaccttt tttgtttttt caaaatagaa aagtattag tggtttatca gcaaaaaagt   2100
ccaattttaa tttagtaaat gttatccttat actgtacaat aaaaacattg cctttgaatg   2160
ttaatttttt ggtacaaaaa taaatttata tgaaaacctg c                       2201
```

```
SEQ ID NO: 3               moltype = AA   length = 5
FEATURE                    Location/Qualifiers
source                     1..5
                           mol_type = protein
                           organism = synthetic construct
SEQUENCE: 3
SYAMS                                                              5

SEQ ID NO: 4               moltype = AA   length = 16
FEATURE                    Location/Qualifiers
source                     1..16
                           mol_type = protein
                           organism = synthetic construct
SEQUENCE: 4
GITGSGGSTY YADSVK                                                  16

SEQ ID NO: 5               moltype = AA   length = 13
FEATURE                    Location/Qualifiers
source                     1..13
                           mol_type = protein
                           organism = synthetic construct
SEQUENCE: 5
DPGTTVIMSW FDP                                                     13

SEQ ID NO: 6               moltype = AA   length = 12
FEATURE                    Location/Qualifiers
source                     1..12
                           mol_type = protein
                           organism = synthetic construct
SEQUENCE: 6
RASQSVRGRY LA                                                      12

SEQ ID NO: 7               moltype = AA   length = 7
FEATURE                    Location/Qualifiers
source                     1..7
                           mol_type = protein
                           organism = synthetic construct
SEQUENCE: 7
GASSRAT                                                            7

SEQ ID NO: 8               moltype = AA   length = 9
FEATURE                    Location/Qualifiers
source                     1..9
                           mol_type = protein
                           organism = synthetic construct
SEQUENCE: 8
QQYGSSPRT                                                          9

SEQ ID NO: 9               moltype = AA   length = 122
FEATURE                    Location/Qualifiers
source                     1..122
                           mol_type = protein
                           organism = synthetic construct
SEQUENCE: 9
```

```
EVQLLESGGG LVQPGGSLRL SCAASGFTFS SYAMSWVRQA PGKGLEWVSG ITGSGGSTYY    60
ADSVKGRFTI SRDNSKNTLY LQMNSLRAED TAVYYCAKDP GTTVIMSWFD PWGQGTLVTV   120
SS                                                                  122

SEQ ID NO: 10           moltype = AA   length = 108
FEATURE                 Location/Qualifiers
source                  1..108
                        mol_type = protein
                        organism = synthetic construct
SEQUENCE: 10
EIVLTQSPGT LSLSPGERAT LSCRASQSVR GRYLAWYQQK PGQAPRLLIY GASSRATGIP    60
DRFSGSGSGT DFTLTISRLE PEDFAVFYCQ QYGSSPRTFG QGTKVEIK               108

SEQ ID NO: 11           moltype = AA   length = 448
FEATURE                 Location/Qualifiers
source                  1..448
                        mol_type = protein
                        organism = synthetic construct
SEQUENCE: 11
EVQLLESGGG LVQPGGSLRL SCAASGFTFS SYAMSWVRQA PGKGLEWVSG ITGSGGSTYY    60
ADSVKGRFTI SRDNSKNTLY LQMNSLRAED TAVYYCAKDP GTTVIMSWFD PWGQGTLVTV   120
SSASTKGPSV FPLAPCSRST SESTAALGCL VKDYFPEPVT VSWNSGALTS GVHTFPAVLQ   180
SSGLYSLSSV VTVPSSNFGT QTYTCNVDHK PSNTKVDKTV ERKCCVECPP CPAPPVAGPS   240
VFLFPPKPKD TLMISRTPEV TCVVVDVSHE DPEVQFNWYV DGVEVHNAKT KPREEQFNST   300
FRVVSVLTVV HQDWLNGKEY KCKVSNKGLP APIEKTISKT KGQPREPQVY TLPPSREEMT   360
KNQVSLTCLV KGFYPSDIAV EWESNGQPEN NYKTTPPMLD SDGSFFLYSK LTVDKSRWQQ   420
GNVFSCSVMH EALHNHYTQK SLSLSPGK                                     448

SEQ ID NO: 12           moltype = AA   length = 215
FEATURE                 Location/Qualifiers
source                  1..215
                        mol_type = protein
                        organism = synthetic construct
SEQUENCE: 12
EIVLTQSPGT LSLSPGERAT LSCRASQSVR GRYLAWYQQK PGQAPRLLIY GASSRATGIP    60
DRFSGSGSGT DFTLTISRLE PEDFAVFYCQ QYGSSPRTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 13           moltype = AA   length = 5
FEATURE                 Location/Qualifiers
source                  1..5
                        mol_type = protein
                        organism = synthetic construct
SEQUENCE: 13
NSGMH                                                                5

SEQ ID NO: 14           moltype = AA   length = 17
FEATURE                 Location/Qualifiers
source                  1..17
                        mol_type = protein
                        organism = synthetic construct
SEQUENCE: 14
VIWYDGSKRY YADSVKG                                                  17

SEQ ID NO: 15           moltype = AA   length = 4
FEATURE                 Location/Qualifiers
source                  1..4
                        mol_type = protein
                        organism = synthetic construct
SEQUENCE: 15
NDDY                                                                4

SEQ ID NO: 16           moltype = AA   length = 11
FEATURE                 Location/Qualifiers
source                  1..11
                        mol_type = protein
                        organism = synthetic construct
SEQUENCE: 16
RASQSVSSYL A                                                        11

SEQ ID NO: 17           moltype = AA   length = 7
FEATURE                 Location/Qualifiers
source                  1..7
                        mol_type = protein
                        organism = synthetic construct
SEQUENCE: 17
DASNRAT                                                             7
```

-continued

```
SEQ ID NO: 18            moltype = AA   length = 9
FEATURE                  Location/Qualifiers
source                   1..9
                         mol_type = protein
                         organism = synthetic construct
SEQUENCE: 18
QQSSNWPRT                                                             9

SEQ ID NO: 19            moltype = AA   length = 113
FEATURE                  Location/Qualifiers
source                   1..113
                         mol_type = protein
                         organism = synthetic construct
SEQUENCE: 19
QVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTLVT VSS          113

SEQ ID NO: 20            moltype = AA   length = 107
FEATURE                  Location/Qualifiers
source                   1..107
                         mol_type = protein
                         organism = synthetic construct
SEQUENCE: 20
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ SSNWPRTFGQ GTKVEIK                 107

SEQ ID NO: 21            moltype = AA   length = 440
FEATURE                  Location/Qualifiers
source                   1..440
                         mol_type = protein
                         organism = synthetic construct
SEQUENCE: 21
QVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTLVT VSSASTKGPS   120
VFPLAPCSRS TSESTAALGC LVKDYFPEPV TVSWNSGALT SGVHTFPAVL QSSGLYSLSS   180
VVTVPSSSLG TKTYTCNVDH KPSNTKVDKR VESKYGPPCP PCPAPEFLGG PSVFLFPPKP   240
KDTLMISRTP EVTCVVVDVS QEDPEVQFNW YVDGVEVHNA KTKPREEQFN STYRVVSVLT   300
VLHQDWLNGK EYKCKVSNKG LPSSIEKTIS KAKGQPREPQ VYTLPPSQEE MTKNQVSLTC   360
LVKGFYPSDI AVEWESNGQP ENNYKTTPPV LDSDGSFFLY SRLTVDKSRW QEGNVFSCSV   420
MHEALHNHYT QKSLSLSLGK                                              440

SEQ ID NO: 22            moltype = AA   length = 214
FEATURE                  Location/Qualifiers
source                   1..214
                         mol_type = protein
                         organism = synthetic construct
SEQUENCE: 22
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ SSNWPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 23            moltype = AA   length = 5
FEATURE                  Location/Qualifiers
source                   1..5
                         mol_type = protein
                         organism = synthetic construct
SEQUENCE: 23
NYYMY                                                                 5

SEQ ID NO: 24            moltype = AA   length = 17
FEATURE                  Location/Qualifiers
source                   1..17
                         mol_type = protein
                         organism = synthetic construct
SEQUENCE: 24
GINPSNGGTN FNEKFKN                                                   17

SEQ ID NO: 25            moltype = AA   length = 11
FEATURE                  Location/Qualifiers
source                   1..11
                         mol_type = protein
                         organism = synthetic construct
SEQUENCE: 25
RDYRFDMGFD Y                                                         11

SEQ ID NO: 26            moltype = AA   length = 15
FEATURE                  Location/Qualifiers
source                   1..15
```

-continued

```
                          mol_type = protein
                          organism = synthetic construct
SEQUENCE: 26
RASKGVSTSG YSYLH                                               15

SEQ ID NO: 27            moltype = AA   length = 7
FEATURE                  Location/Qualifiers
source                   1..7
                          mol_type = protein
                          organism = synthetic construct
SEQUENCE: 27
LASYLES                                                        7

SEQ ID NO: 28            moltype = AA   length = 9
FEATURE                  Location/Qualifiers
source                   1..9
                          mol_type = protein
                          organism = synthetic construct
SEQUENCE: 28
QHSRDLPLT                                                      9

SEQ ID NO: 29            moltype = AA   length = 120
FEATURE                  Location/Qualifiers
source                   1..120
                          mol_type = protein
                          organism = synthetic construct
SEQUENCE: 29
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120

SEQ ID NO: 30            moltype = AA   length = 111
FEATURE                  Location/Qualifiers
source                   1..111
                          mol_type = protein
                          organism = synthetic construct
SEQUENCE: 30
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI K            111

SEQ ID NO: 31            moltype = AA   length = 447
FEATURE                  Location/Qualifiers
source                   1..447
                          mol_type = protein
                          organism = synthetic construct
SEQUENCE: 31
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 32            moltype = AA   length = 218
FEATURE                  Location/Qualifiers
source                   1..218
                          mol_type = protein
                          organism = synthetic construct
SEQUENCE: 32
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218
```

METHODS FOR THE TREATMENT OF MELANOMA USING COMPOSITIONS OF DENOSUMAB AND PD-1 INHIBITOR

CROSS-REFERENCE TO RELATED APPLICATIONS

This application is a continuation of International Patent Application No. PCT/US2023/074871, filed Sep. 22, 2023, which claims the benefit of U.S. Provisional Patent Application No. 63/409,348, filed Sep. 23, 2022, each of which is hereby incorporated by reference in its entirety.

INCORPORATION BY REFERENCE OF MATERIALS SUBMITTED ELECTRONICALLY

This application contains, as a separate part of the disclosure, a Sequence Listing in computer readable form (Filename: 58296_SeqListing.xml; Size: 33,764 bytes; Created Sep. 22, 2023), which is incorporated by reference in its entirety.

TECHNICAL FIELD

The disclosure relates to materials and methods for treating melanoma in a subject in need thereof.

BACKGROUND

Melanoma is a type of skin cancer characterized by malignant transformation of pigment-producing cells known as melanocytes. Melanomas typically occur in the skin, but may also occur in the mucosal membranes (nose, vagina, rectum) or eye. Although rarer than other types of skin cancer such as squamous cell carcinoma and basal cell carcinoma, melanoma is more likely to metastasize and disproportionately contributes to deaths from skin cancer. Specifically, while melanoma accounts for less than 5% of skin cancer cases, it is responsible for about 80% of skin cancer-related deaths. Although the average age of patients diagnosed with melanoma is 63 years old, melanoma is also a common cancer in young adults.

The American Cancer Society estimated that approximately 99,780 new cases of cutaneous melanoma (CM) and 7,650 melanoma related deaths would occur in the United States in 2022 (Siegel R L, Miller K D, Fuchs H E, Jemal A: Cancer Statistics, 2022. CA Cancer J Clin 72:7-33, 2022). Early detection and treatment significantly impact long-term prognosis as overall survival (OS) drops precipitously for patients diagnosed with melanomas that are locally advanced and/or distant metastatic. The 5-year OS rate is about 28% to 30% for patients diagnosed with stage IV melanoma in comparison to patients with early-stage tumors (Stage IA to IIB), who exhibit 5-year survival rates in the 87% to 99% range (Siegel R L, Miller K D, Fuchs H E, Jemal A: Cancer Statistics, 2022. CA Cancer J Clin 72:7-33, 2022). Unfortunately, a proportion of metastatic CMs remain difficult to treat despite the introduction of novel therapies for this disease over the last decade, and surgical resection is generally not a curative treatment option. Accordingly, there is a need in the art for alternative methods of treating melanomas that are locally advanced (i.e., stage III) and/or distant metastatic (i.e., stage IV melanoma).

SUMMARY

Provided herein are methods of treating melanoma, such as, e.g., stage III/IV cutaneous or mucosal melanoma, in a subject in need thereof, comprising administering a therapeutically effective amount of denosumab to the subject and optionally co-administering a therapeutically effective amount of a PD-1 inhibitor to the subject. Also provided herein are uses of denosumab or a PD-1 inhibitor in the manufacture of a medicament adapted for use in a method described herein, as well as pharmaceutical compositions comprising denosumab and/or a PD-1 inhibitor for use in a method described herein.

Disclosed herein is a method of treating melanoma in a subject in need thereof, comprising administering a therapeutically effective amount of denosumab to the subject, wherein: the subject does not have bone metastases; and the subject does not have hypercalcemia.

Denosumab is a human IgG2 monoclonal antibody that binds to soluble RANKL and is indicated for treatment or prevention of skeletal complications from bone metastases of any solid tumor malignancy. RANKL augments thymic tolerance by upregulating the transcription factor autoimmune regulator, AIRE, in the thymus. In syngeneic melanoma mice, RANKL blockade increases anti-melanoma immunity by rescuing melanoma-specific T cells from thymic deletion and augments antitumor responses when combined with CTLA4±PD-1 blockade (Bakhru, JCI Insight 2(18):e93265, 2017).

In some embodiments, a baseline tumor tissue sample from the subject comprises brisk tumor-infiltrating lymphocytes (TILs). TILs may be detected in a variety of ways including ematoxylin and eosin (H-E)-stained tumor sections. In some embodiments, a baseline peripheral blood sample from the subject comprises high serum-free RANKL and/or low serum osteoprotegerin (OPG) levels as assessed by flow cytometric analysis. In some embodiments, a baseline tumor tissue sample from the subject expresses two or more of Sox10, RANK, and OPG as assessed by immunohistochemistry.

In some embodiments, the subject has not previously received a PD-1 inhibitor. In some embodiments, the subject previously received a PD-1 inhibitor in stage III or stage IV (stage III/IV) melanoma and the interval between the last dose of the PD-1 inhibitor and the date of relapse is at least about one year.

Programmed Death-Ligand 1 (PD-L1) is expressed on approximately 40-50% of melanomas and has limited expression in most visceral organs, with the exception of respiratory epithelium and placental tissue (Johnson et al., Nivolumab in melanoma: latest evidence and clinical potential. Therapeutic Advances in Medical Oncology 7:97-106, 2015). Pembrolizumab is an IgG4 kappa immunoglobulin that blocks the interaction between PD-1 and PD-L1, which decreases proliferation of T cells and production of cytokines. Pembrolizumab is approved by the United States Food and Drug Administration (FDA) for upfront treatment of unresectable stage III or distant metastatic melanoma (AJCC stage III/IV) (Robert et al, Pembrolizumab versus Ipilimumab in Advanced Melanoma., N Engl J Med 372:2521-32, 2015). Nivolumab is a fully humanized monoclonal antibody of the immunoglobulin IgG4 that directly blocks the interaction between PD-1 and its ligands, PD-L1 and PD-L2. This blockade enhances functional activity of the target lymphocytes to facilitate an antitumor immune response, leading to immune-mediated tumor regression. The FDA has approved nivolumab as an adjuvant treatment for patients with completely resected melanoma with lymph node involvement or metastatic disease, based on findings from the phase III CheckMate-238 trial.

In some embodiments, the subject is administered one or more (e.g., one, two, three, four) loading doses of denosumab. In some embodiments, the subject is administered one loading dose of denosumab. In some embodiments, the subject is administered two loading doses of denosumab.

In some embodiments, the one or more loading doses of denosumab each independently comprise one or more unit doses, each unit dose independently comprising about 45 mg to about 120 mg of denosumab.

In some embodiments, the one or more loading doses of denosumab are equivalent to:

a first loading dose comprising about 120 mg of denosumab administered on day 1; and a second loading dose comprising about 120 mg of denosumab administered on about day 8.

In some embodiments, the one or more loading doses of denosumab comprise:

a first loading dose comprising about 120 mg of denosumab administered on day 1; and a second loading dose comprising about 120 mg of denosumab administered on about day 8.

In some embodiments, the therapeutically effective amount of denosumab comprises one or more unit doses, each administered at about 4 week intervals, each unit dose independently comprising about 45 mg to about 120 mg of denosumab. In some embodiments, the therapeutically effective amount of denosumab is equivalent to about 120 mg of denosumab administered once every about 4 weeks. In some embodiments, the therapeutically effective amount of denosumab is about 120 mg of denosumab, administered in one or more unit doses at about 4 week intervals. In some embodiments, the therapeutically effective amount of denosumab is about 120 mg of denosumab, administered in one unit dose at about 4 week intervals.

In some embodiments, the administration is associated with an anti-tumor immune response and/or a tumor objective response. In some embodiments, the administration is associated with an anti-tumor immune response, representative examples of which are provided below. In some embodiments, the administration is associated with a tumor objective response, representative examples of which are provided below. In some embodiments, the administration is associated with an anti-tumor immune response and a tumor objective response.

In some embodiments, the anti-tumor immune response is chosen from:

a change (e.g., an increase) in recent thymic emigrant cells (RTEs) in a peripheral blood sample from the subject relative to a baseline peripheral blood sample;

a change (e.g., an increase) in density of tumor-infiltrating cluster of differentiation (CD8+) cells (TILs) in a tumor tissue sample from the subject relative to a baseline tumor tissue sample;

an increase in the number of tumor-infiltrating CD8+ cells in a tumor tissue sample from the subject relative to a baseline tumor tissue sample as assessed by immunohistochemistry;

an increase in tumor cell death in a tumor tissue sample from the subject relative to a baseline tumor tissue sample as assessed by immunohistochemistry;

an increase in the total number of CD8+ and CD4+ non-$T_{reg}$ RTEs in a peripheral blood sample from the subject relative to a baseline peripheral blood sample as assessed by flow cytometric analysis;

an increase in the total number of CD4+ $T_{reg}$ cells in a peripheral blood sample from the subject relative to a baseline peripheral blood sample as assessed by flow cytometric analysis;

an increase in immune cell clonal diversity in a peripheral blood sample from the subject relative to a baseline peripheral blood sample as assessed by flow cytometric analysis;

an increase in the number of RANK+ $T_{reg}$ cells in a peripheral blood sample from the subject relative to a baseline peripheral blood sample as assessed by flow cytometric analysis;

at least partial suppression of myeloid-derived suppressor cells (MDSCs) in a peripheral blood sample from the subject relative to a baseline peripheral blood sample as assessed by flow cytometric analysis;

a decrease in the number of tumor-associated macrophages in a tumor tissue sample from the subject relative to a baseline tumor tissue sample; and a decrease in the number of tumor-infiltrating MDSCs in a tumor tissue sample from the subject relative to a baseline tumor tissue sample. Any one or more of these parameters is contemplated.

In some embodiments, the anti-tumor immune response is an increase in recent thymic emigrant cells (RTEs) in a peripheral blood sample from the subject relative to a baseline peripheral blood sample. In some embodiments, the anti-tumor immune response is a change (e.g., an increase) in density of tumor-infiltrating cluster of differentiation (CD8+) cells (TILs) in a tumor tissue sample from the subject relative to a baseline tumor tissue sample. In some embodiments, the anti-tumor immune response is an increase in the number of tumor-infiltrating CD8+ cells in a tumor tissue sample from the subject relative to a baseline tumor tissue sample as assessed by immunohistochemistry. In some embodiments, the anti-tumor immune response is an increase in tumor cell death in a tumor tissue sample from the subject relative to a baseline tumor tissue sample as assessed by immunohistochemistry. In some embodiments, the anti-tumor immune response is an increase in the total number of CD8+ and CD4+ non-Treg RTEs in a peripheral blood sample from the subject relative to a baseline peripheral blood sample as assessed by flow cytometric analysis. In some embodiments, the anti-tumor immune response is an increase in the total number of CD4+ Treg cells in a peripheral blood sample from the subject relative to a baseline peripheral blood sample as assessed by flow cytometric analysis. In some embodiments, the anti-tumor immune response is an increase in immune cell clonal diversity in a peripheral blood sample from the subject relative to a baseline peripheral blood sample as assessed by flow cytometric analysis. In some embodiments, the anti-tumor immune response is an increase in the number of RANK+ Treg cells in a peripheral blood sample from the subject relative to a baseline peripheral blood sample as assessed by flow cytometric analysis. In some embodiments, the anti-tumor immune response is at least partial suppression of myeloid-derived suppressor cells (MDSCs) in a peripheral blood sample from the subject relative to a baseline peripheral blood sample as assessed by flow cytometric analysis. In some embodiments, the anti-tumor immune response is a decrease in the number of tumor-associated macrophages in a tumor tissue sample from the subject relative to a baseline tumor tissue sample. In some embodiments, the anti-tumor immune response is a decrease in the number of tumor-infiltrating MDSCs in a tumor tissue sample from the subject relative to a baseline tumor tissue sample.

In some embodiments, the tumor objective response is a Complete Response or Partial Response as assessed using RECIST v1.1 criteria. In some embodiments, the tumor objective response is a Complete Response as assessed using RECIST v1.1 criteria. In some embodiments, the tumor objective response is a Partial Response as assessed using RECIST v1.1 criteria.

In some embodiments, the melanoma is cutaneous melanoma or mucosal melanoma. In some embodiments, the melanoma is cutaneous melanoma. In some embodiments, the melanoma is mucosal melanoma.

In some embodiments, the melanoma is stage III melanoma or stage IV melanoma. In some embodiments, the melanoma is stage III melanoma. In some embodiments, the melanoma is stage IV melanoma. In some embodiments, the melanoma is American Joint Committee on Cancer (AJCC) stage III melanoma or AJCC stage IV melanoma. In some embodiments, the melanoma is AJCC stage III melanoma. In some embodiments, the melanoma is AJCC stage IV melanoma. In some embodiments, the melanoma is unresectable. In some embodiments, the melanoma is resectable stage III melanoma.

In some embodiments, the subject is not co-administered an anti-CTLA4 agent. In some embodiments, the subject is not co-administered ipilimumab.

In some embodiments, denosumab is administered to the subject by injection. In some embodiments, denosumab is administered to the subject by subcutaneous injection. In some embodiments, denosumab is administered to the subject by injection into the upper arm, upper thigh, or abdomen of the subject. In some embodiments, denosumab is administered to the subject by subcutaneous injection into the upper arm, upper thigh, or abdomen of the subject.

In some embodiments, the subject does not exhibit a dose limiting toxicity (DLT) during denosumab administration. In some embodiments, the subject does not exhibit any grade 3 or grade 4 adverse events associated with denosumab during denosumab administration. In some embodiments, the subject is not hypocalcemic during denosumab administration.

In some embodiments, the subject is administered denosumab for at least 12 weeks. In some embodiments, the subject is administered denosumab for at least 24 weeks. In some embodiments, the subject is administered denosumab for at least 48 weeks. In some embodiments, the subject is administered denosumab for at most one year.

In some embodiments, the subject is co-administered a PD-1 inhibitor. In some embodiments, the first dose of the PD-1 inhibitor is administered within about 24 hours of a third loading dose comprising about 120 mg of denosumab administered on about day 22. In some embodiments, the first dose of the PD-1 inhibitor and a concomitant dose of denosumab are co-administered on about day 22. In some embodiments, the concomitant dose of denosumab is about 120 mg of denosumab.

In some embodiments, the PD-1 inhibitor is chosen from pembrolizumab, nivolumab, cemiplimab, dostarlimab, atezolizumab, avelumab, and durvalumab. In some embodiments, the PD-1 inhibitor is chosen from pembrolizumab and nivolumab. In some embodiments, the PD-1 inhibitor is pembrolizumab. In some embodiments, the PD-1 inhibitor is nivolumab.

In some embodiments, when the PD-1 inhibitor and denosumab are each administered to the subject on the same day, the PD-1 inhibitor is administered to the subject prior to denosumab administration.

Also disclosed herein is a method of treating melanoma in a subject in need thereof, comprising administering a therapeutically effective amount of denosumab to the subject, wherein a baseline tumor tissue sample from the subject comprises brisk tumor-infiltrating lymphocytes (TILs).

In some embodiments, a baseline peripheral blood sample from the subject comprises high serum-free RANKL and/or low serum OPG levels as assessed by flow cytometric analysis. In some embodiments, a baseline tumor tissue sample from the subject expresses two or more of Sox10, RANK, and OPG as assessed by immunohistochemistry.

In some embodiments, the subject does not have bone metastases, and/or the subject does not have hypercalcemia. In some embodiments, the subject does not have bone metastases. In some embodiments, the subject does not have hypercalcemia.

In some embodiments, the subject has not previously received a PD-1 inhibitor. In some embodiments, the subject previously received a PD-1 inhibitor in stage III or stage IV melanoma and the interval between the last dose of the PD-1 inhibitor and the date of relapse is at least about one year.

In some embodiments, the subject is administered one or more (e.g., one, two, three, four) loading doses of denosumab. In some embodiments, the subject is administered one loading dose of denosumab. In some embodiments, the subject is administered two loading doses of denosumab.

In some embodiments, the one or more loading doses of denosumab each independently comprise one or more unit doses, each unit dose independently comprising about 45 mg to about 120 mg of denosumab.

In some embodiments, the one or more loading doses of denosumab are equivalent to:

a first loading dose comprising about 120 mg of denosumab administered on day 1; and a second loading dose comprising about 120 mg of denosumab administered on about day 8.

In some embodiments, the one or more loading doses of denosumab comprise:

a first loading dose comprising about 120 mg of denosumab administered on day 1; and a second loading dose comprising about 120 mg of denosumab administered on about day 8.

In some embodiments, the first dose of the PD-1 inhibitor is administered within about 24 hours of a third loading dose comprising about 120 mg of denosumab administered on about day 22.

In some embodiments, the first dose of the PD-1 inhibitor and a concomitant dose of denosumab are co-administered on about day 22. In some embodiments, the concomitant dose of denosumab is about 120 mg of denosumab.

In some embodiments, the therapeutically effective amount of denosumab comprises one or more unit doses, each administered at about 4 week intervals, each unit dose independently comprising about 45 mg to about 120 mg of denosumab. In some embodiments, the therapeutically effective amount of denosumab is equivalent to about 120 mg of denosumab administered once every about 4 weeks. In some embodiments, the therapeutically effective amount of denosumab is about 120 mg of denosumab, administered in one or more unit doses at about 4 week intervals. In some embodiments, the therapeutically effective amount of denosumab is about 120 mg of denosumab, administered in one unit dose at about 4 week intervals.

In some embodiments, the administration is associated with an anti-tumor immune response and/or a tumor objective response. In some embodiments, the administration is associated with an anti-tumor immune response, representative examples of which are set forth below. In some embodiments, the administration is associated with a tumor objective response, representative examples of which are set forth below. In some embodiments, the administration is associated with an anti-tumor immune response and a tumor objective response.

In some embodiments, the anti-tumor immune response is chosen from:

a change (e.g., an increase) in recent thymic emigrant cells (RTEs) in a peripheral blood sample from the subject relative to a baseline peripheral blood sample;

a change (e.g., an increase) in density of tumor-infiltrating cluster of differentiation (CD8+) cells (TILs) in a tumor tissue sample from the subject relative to a baseline tumor tissue sample;

an increase in the number of tumor-infiltrating CD8+ cells in a tumor tissue sample from the subject relative to a baseline tumor tissue sample as assessed by immunohistochemistry;

an increase in tumor cell death in a tumor tissue sample from the subject relative to a baseline tumor tissue sample as assessed by immunohistochemistry;

an increase in the total number of CD8+ and CD4+ non-$T_{reg}$ RTEs in a peripheral blood sample from the subject relative to a baseline peripheral blood sample as assessed by flow cytometric analysis;

an increase in the total number of CD4+ $T_{reg}$ cells in a peripheral blood sample from the subject relative to a baseline peripheral blood sample as assessed by flow cytometric analysis;

an increase in immune cell clonal diversity in a peripheral blood sample from the subject relative to a baseline peripheral blood sample as assessed by flow cytometric analysis;

an increase in the number of RANK+ $T_{reg}$ cells in a peripheral blood sample from the subject relative to a baseline peripheral blood sample as assessed by flow cytometric analysis;

at least partial suppression of myeloid-derived suppressor cells (MDSCs) in a peripheral blood sample from the subject relative to a baseline peripheral blood sample as assessed by flow cytometric analysis;

a decrease in the number of tumor-associated macrophages in a tumor tissue sample from the subject relative to a baseline tumor tissue sample; and a decrease in the number of tumor-infiltrating MDSCs in a tumor tissue sample from the subject relative to a baseline tumor tissue sample. Any one or more of these parameters are contemplated.

In some embodiments, the anti-tumor immune response is an increase in recent thymic emigrant cells (RTEs) in a peripheral blood sample from the subject relative to a baseline peripheral blood sample. In some embodiments, the anti-tumor immune response is a change (e.g., an increase) in density of tumor-infiltrating cluster of differentiation (CD8+) cells (TILs) in a tumor tissue sample from the subject relative to a baseline tumor tissue sample. In some embodiments, the anti-tumor immune response is an increase in the number of tumor-infiltrating CD8+ cells in a tumor tissue sample from the subject relative to a baseline tumor tissue sample as assessed by immunohistochemistry. In some embodiments, the anti-tumor immune response is an increase in tumor cell death in a tumor tissue sample from the subject relative to a baseline tumor tissue sample as assessed by immunohistochemistry. In some embodiments, the anti-tumor immune response is an increase in the total number of CD8+ and CD4+ non-$T_{reg}$ RTEs in a peripheral blood sample from the subject relative to a baseline peripheral blood sample as assessed by flow cytometric analysis. In some embodiments, the anti-tumor immune response is an increase in the total number of CD4+ $T_{reg}$ cells in a peripheral blood sample from the subject relative to a baseline peripheral blood sample as assessed by flow cytometric analysis. In some embodiments, the anti-tumor immune response is an increase in immune cell clonal diversity in a peripheral blood sample from the subject relative to a baseline peripheral blood sample as assessed by flow cytometric analysis. In some embodiments, the anti-tumor immune response is an increase in the number of RANK+ $T_{reg}$ cells in a peripheral blood sample from the subject relative to a baseline peripheral blood sample as assessed by flow cytometric analysis. In some embodiments, the anti-tumor immune response is at least partial suppression of myeloid-derived suppressor cells (MDSCs) in a peripheral blood sample from the subject relative to a baseline peripheral blood sample as assessed by flow cytometric analysis. In some embodiments, the anti-tumor immune response is a decrease in the number of tumor-associated macrophages in a tumor tissue sample from the subject relative to a baseline tumor tissue sample. In some embodiments, the anti-tumor immune response is a decrease in the number of tumor-infiltrating MDSCs in a tumor tissue sample from the subject relative to a baseline tumor tissue sample.

In some embodiments, the tumor objective response is a Complete Response (CR) or Partial Response (PR) as assessed using RECIST v1.1 criteria. In some embodiments, the tumor objective response is a Complete Response as assessed using RECIST v1.1 criteria. In some embodiments, the tumor objective response is a Partial Response as assessed using RECIST v1.1 criteria.

In some embodiments, the melanoma is cutaneous melanoma (CM) or mucosal melanoma (MM). In some embodiments, the melanoma is cutaneous melanoma. In some embodiments, the melanoma is mucosal melanoma.

In some embodiments, the melanoma is stage III melanoma or stage IV melanoma. In some embodiments, the melanoma is stage III melanoma. In some embodiments, the melanoma is stage IV melanoma. In some embodiments, the melanoma is American Joint Committee on Cancer (AJCC) stage III melanoma or AJCC stage IV melanoma. In some embodiments, the melanoma is AJCC stage III melanoma. In some embodiments, the melanoma is AJCC stage IV melanoma. In some embodiments, the melanoma is unresectable. In some embodiments, the melanoma is resectable stage III melanoma.

In some embodiments, the subject is not co-administered an anti-CTLA4 agent. In some embodiments, the subject is not co-administered ipilimumab.

In some embodiments, denosumab is administered to the subject by injection. In some embodiments, denosumab is administered to the subject by subcutaneous (sc) injection. In some embodiments, denosumab is administered to the subject by injection into the upper arm, upper thigh, or abdomen of the subject. In some embodiments, denosumab is administered to the subject by subcutaneous injection into the upper arm, upper thigh, or abdomen of the subject.

In some embodiments, the subject does not exhibit a dose limiting toxicity (DLT) during denosumab administration. In some embodiments, the subject does not exhibit any grade 3 or grade 4 adverse events associated with denosumab during denosumab administration. In some embodiments, the subject is not hypocalcemic during denosumab administration.

In some embodiments, the subject is administered denosumab for at least 12 weeks. In some embodiments, the subject is administered denosumab for at least 24 weeks. In some embodiments, the subject is administered denosumab for at least 48 weeks. In some embodiments, the subject is administered denosumab for at most one year.

In some embodiments, the subject is co-administered a PD-1 inhibitor. In some embodiments, the first dose of the PD-1 inhibitor is administered within about 24 hours of a third loading dose comprising about 120 mg of denosumab administered on about day 22. In some embodiments, the first dose of the PD-1 inhibitor and a concomitant dose of denosumab are co-administered on about day 22. In some embodiments, the concomitant dose of denosumab is about 120 mg of denosumab.

In some embodiments, the PD-1 inhibitor is chosen from pembrolizumab, nivolumab, cemiplimab, dostarlimab, atezolizumab, avelumab, and durvalumab. In some embodiments, the PD-1 inhibitor is chosen from pembrolizumab and nivolumab. In some embodiments, the PD-1 inhibitor is pembrolizumab. In some embodiments, the PD-1 inhibitor is nivolumab.

In some embodiments, when the PD-1 inhibitor and denosumab are each administered to the subject on the same day, the PD-1 inhibitor is administered to the subject prior to denosumab administration.

Also disclosed herein is a method of treating melanoma in a subject in need thereof, comprising co-administering a therapeutically effective amount of denosumab and a therapeutically effective amount of a PD 1 inhibitor to the subject, wherein:

one or more loading doses of denosumab are administered to the subject prior to the first dose of the PD-1 inhibitor; and the co-administration is associated with an anti-tumor immune response and/or a tumor objective response.

In some embodiments, the PD-1 inhibitor is chosen from pembrolizumab, nivolumab, cemiplimab, dostarlimab, atezolizumab, avelumab, and durvalumab. In some embodiments, the PD-1 inhibitor is chosen from pembrolizumab and nivolumab. In some embodiments, the PD-1 inhibitor is pembrolizumab. In some embodiments, the PD-1 inhibitor is nivolumab.

In some embodiments, a baseline tumor tissue sample from the subject comprises brisk tumor-infiltrating lymphocytes (TILs). In some embodiments, a baseline peripheral blood sample from the subject comprises high serum-free RANKL and/or low serum OPG levels as assessed by flow cytometric analysis. In some embodiments, a baseline tumor tissue sample from the subject expresses two or more of Sox10, RANK, and OPG as assessed by immunohistochemistry.

In some embodiments, the subject has not previously received a PD-1 inhibitor. In some embodiments, the subject previously received a PD-1 inhibitor in stage III or stage IV melanoma and the interval between the last dose of the PD-1 inhibitor and the date of relapse is at least about one year.

In some embodiments, the subject does not have bone metastases, and/or the subject does not have hypercalcemia. In some embodiments, the subject does not have bone metastases. In some embodiments, the subject does not have hypercalcemia.

In some embodiments, the subject is administered one or more (e.g., one, two, three, four) loading doses of denosumab. In some embodiments, the subject is administered one loading dose of denosumab. In some embodiments, the subject is administered two loading doses of denosumab.

In some embodiments, the one or more loading doses of denosumab each independently comprise one or more unit doses, each unit dose independently comprising about 45 mg to about 120 mg of denosumab.

In some embodiments, the one or more loading doses of denosumab are equivalent to:

a first loading dose comprising about 120 mg of denosumab administered on day 1; and a second loading dose comprising about 120 mg of denosumab administered on about day 8.

In some embodiments, the one or more loading doses of denosumab comprise:

a first loading dose comprising about 120 mg of denosumab administered on day 1; and a second loading dose comprising about 120 mg of denosumab administered on about day 8.

In some embodiments, the first dose of the PD-1 inhibitor is administered within about 24 hours of a third loading dose comprising about 120 mg of denosumab administered on about day 22. In some embodiments, the first dose of the PD-1 inhibitor and a concomitant dose of denosumab are co-administered on about day 22. In some embodiments, the concomitant dose of denosumab is about 120 mg of denosumab.

In some embodiments, the therapeutically effective amount of denosumab comprises one or more unit doses, each administered at about 4 week intervals, each unit dose independently comprising about 45 mg to about 120 mg of denosumab. In some embodiments, the therapeutically effective amount of denosumab is equivalent to about 120 mg of denosumab administered once every about 4 weeks. In some embodiments, the therapeutically effective amount of denosumab is about 120 mg of denosumab, administered in one or more unit doses at about 4 week intervals. In some embodiments, the therapeutically effective amount of denosumab is about 120 mg of denosumab, administered in one unit dose at about 4 week intervals.

In some embodiments, the PD-1 inhibitor is pembrolizumab; and the therapeutically effective amount of the PD-1 inhibitor is equivalent to about 200 mg of pembrolizumab administered at about 3 week intervals.

In some embodiments, the PD-1 inhibitor is pembrolizumab; and the therapeutically effective amount of the PD-1 inhibitor comprises about 200 mg of pembrolizumab administered at about 3 week intervals.

In some embodiments, the PD-1 inhibitor is nivolumab; and the therapeutically effective amount of the PD-1 inhibitor is equivalent to about 480 mg of nivolumab administered at about 4 week intervals.

In some embodiments, the PD-1 inhibitor is nivolumab; and the therapeutically effective amount of the PD-1 inhibitor comprises about 480 mg of nivolumab administered at about 4 week intervals.

In some embodiments, denosumab is administered to the subject by injection. In some embodiments, denosumab is administered to the subject by subcutaneous injection. In some embodiments, denosumab is administered to the subject by injection into the upper arm, upper thigh, or abdomen of the subject. In some embodiments, denosumab is administered to the subject by subcutaneous injection into the upper arm, upper thigh, or abdomen of the subject.

In some embodiments, the PD-1 inhibitor is administered to the subject intravenously.

In some embodiments, when the PD-1 inhibitor and denosumab are each administered to the subject on the same day, the PD-1 inhibitor is administered to the subject prior to denosumab administration.

In some embodiments, the co-administration is associated with an anti-tumor immune response. In some embodiments, the co-administration is associated with a tumor objective response. In some embodiments, the co-administration is associated with an anti-tumor immune response and a tumor objective response.

In some embodiments, the anti-tumor immune response is chosen from:

a change (e.g., an increase) in recent thymic emigrant cells (RTEs) in a peripheral blood sample from the subject relative to a baseline peripheral blood sample;

a change (e.g., an increase) in density of tumor-infiltrating cluster of differentiation (CD8+) cells (TILs) in a tumor tissue sample from the subject relative to a baseline tumor tissue sample;

an increase in the number of tumor-infiltrating CD8+ cells in a tumor tissue sample from the subject relative to a baseline tumor tissue sample as assessed by immuno-histochemistry;

an increase in tumor cell death in a tumor tissue sample from the subject relative to a baseline tumor tissue sample as assessed by immunohistochemistry;

an increase in the total number of CD8+ and CD4+ non-$T_{reg}$ RTEs in a peripheral blood sample from the subject relative to a baseline peripheral blood sample as assessed by flow cytometric analysis;

an increase in the total number of CD4+ $T_{reg}$ cells in a peripheral blood sample from the subject relative to a baseline peripheral blood sample as assessed by flow cytometric analysis;

an increase in immune cell clonal diversity in a peripheral blood sample from the subject relative to a baseline peripheral blood sample as assessed by flow cytometric analysis;

an increase in the number of RANK+ $T_{reg}$ cells in a peripheral blood sample from the subject relative to a baseline peripheral blood sample as assessed by flow cytometric analysis;

at least partial suppression of myeloid-derived suppressor cells (MDSCs) in a peripheral blood sample from the subject relative to a baseline peripheral blood sample as assessed by flow cytometric analysis;

a decrease in the number of tumor-associated macro-phages in a tumor tissue sample from the subject relative to a baseline tumor tissue sample; and a decrease in the number of tumor-infiltrating MDSCs in a tumor tissue sample from the subject relative to a baseline tumor tissue sample. Any one or more of these parameters is contemplated.

In some embodiments, the anti-tumor immune response is an increase in recent thymic emigrant cells (RTEs) in a peripheral blood sample from the subject relative to a baseline peripheral blood sample. In some embodiments, the anti-tumor immune response is a change (e.g., an increase) in density of tumor-infiltrating cluster of differentiation (CD8+) cells (TILs) in a tumor tissue sample from the subject relative to a baseline tumor tissue sample. In some embodiments, the anti-tumor immune response is an increase in the number of tumor-infiltrating CD8+ cells in a tumor tissue sample from the subject relative to a baseline tumor tissue sample as assessed by immunohistochemistry. In some embodiments, the anti-tumor immune response is an increase in tumor cell death in a tumor tissue sample from the subject relative to a baseline tumor tissue sample as assessed by immunohistochemistry. In some embodiments, the anti-tumor immune response is an increase in the total number of CD8+ and CD4+ non-$T_{reg}$ RTEs in a peripheral blood sample from the subject relative to a baseline peripheral blood sample as assessed by flow cytometric analysis. In some embodiments, the anti-tumor immune response is an increase in the total number of CD4+ $T_{reg}$ cells in a peripheral blood sample from the subject relative to a baseline peripheral blood sample as assessed by flow cytometric analysis. In some embodiments, the anti-tumor immune response is an increase in immune cell clonal diversity in a peripheral blood sample from the subject relative to a baseline peripheral blood sample as assessed by flow cytometric analysis. In some embodiments, the anti-tumor immune response is an increase in the number of RANK+ $T_{reg}$ cells in a peripheral blood sample from the subject relative to a baseline peripheral blood sample as assessed by flow cytometric analysis. In some embodiments, the anti-tumor immune response is at least partial suppression of myeloid-derived suppressor cells (MDSCs) in a peripheral blood sample from the subject relative to a baseline peripheral blood sample as assessed by flow cytometric analysis. In some embodiments, the anti-tumor immune response is a decrease in the number of tumor-associated macrophages in a tumor tissue sample from the subject relative to a baseline tumor tissue sample. In some embodiments, the anti-tumor immune response is a decrease in the number of tumor-infiltrating MDSCs in a tumor tissue sample from the subject relative to a baseline tumor tissue sample.

In some embodiments, the tumor objective response is a Complete Response or Partial Response as assessed using RECIST v1.1 criteria. In some embodiments, the tumor objective response is a Complete Response as assessed using RECIST v1.1 criteria. In some embodiments, the tumor objective response is a Partial Response as assessed using RECIST v1.1 criteria.

In some embodiments, the melanoma is cutaneous melanoma or mucosal melanoma. In some embodiments, the melanoma is cutaneous melanoma. In some embodiments, the melanoma is mucosal melanoma.

In some embodiments, the melanoma is stage III melanoma or stage IV melanoma. In some embodiments, the melanoma is stage III melanoma. In some embodiments, the melanoma is stage IV melanoma. In some embodiments, the melanoma is American Joint Committee on Cancer (AJCC) stage III melanoma or AJCC stage IV melanoma. In some embodiments, the melanoma is AJCC stage III melanoma. In some embodiments, the melanoma is AJCC stage IV melanoma. In some embodiments, the melanoma is unresectable. In some embodiments, the melanoma is resectable stage III melanoma.

In some embodiments, the subject is not co-administered an anti-CTLA4 agent. In some embodiments, the subject is not co-administered ipilimumab.

In some embodiments, the subject does not exhibit a dose limiting toxicity (DLT) during the treatment period. In some embodiments, the subject does not exhibit any grade 3 or grade 4 adverse events associated with denosumab during the treatment period. In some embodiments, the subject is not hypocalcemic during the treatment period.

Also disclosed herein is use of denosumab in the manufacture of a medicament adapted for use in a method of treating melanoma in a subject in need thereof. In some embodiments, the method possesses one or more of the features of a method described above.

Also disclosed herein is use of a PD-1 inhibitor in the manufacture of a medicament adapted for use in a method of treating melanoma in a subject in need thereof. In some embodiments, the method possesses one or more of the features of a method described above.

Also disclosed herein is a pharmaceutical composition comprising denosumab for use in a method of treating melanoma in a subject in need thereof. In some embodiments, the method possesses one or more of the features of a method described above.

Also disclosed herein is a pharmaceutical composition comprising a PD-1 inhibitor for use in a method of treating melanoma in a subject in need thereof. In some embodiments, the method possesses one or more of the features of a method described above.

Additional features and variations of the materials and methods of the disclosure will be apparent to those skilled in the art from the entirety of this application, including the figure and detailed description, and all such features are intended as aspects of the disclosure. Features of the disclosure described herein can be re-combined into additional embodiments that also are intended as aspects of the disclosure, irrespective of whether the combination of features is specified as an aspect or embodiment of the disclosure. The entire document is intended to be related as a unified disclosure, and it should be understood that all combinations of features described herein (even if described in separate sections) are contemplated, even if the combination of features is not found together in the same sentence, or paragraph, or section of this document. Also, only such limitations which are described herein as critical to the disclosure should be viewed as such; variations of the disclosure lacking limitations which have not been described herein as critical are intended as aspects of the disclosure.

All references, including publications, patent applications, and patents, cited herein are hereby incorporated by reference to the same extent as if each reference were individually and specifically indicated to be incorporated by reference and were set forth in its entirety herein.

BRIEF DESCRIPTION OF THE DRAWINGS

FIG. 1 is a study schematic for a clinical trial described in Example 1. The following abbreviations are used in the schematic: SC, subcutaneous; D, day; Wk, week; RECIST, Response Evaluation Criteria in Solid Tumors; OS, overall survival; Tx, treatment; AEs, adverse events; pt, patient; PBMC, peripheral blood mononuclear cells; Tregs, T regulatory cells; MDSC, myeloid-derived suppressor cells; TCR, T-cell receptor; OPG, osteoprotegerin; IHC, immunohistochemistry; IF, immunofluorescence.

DETAILED DESCRIPTION

Definitions:

As used herein, the terms "a," "an," "the," and similar referents, in the context of example embodiments and claims, are to be construed as covering both the singular and the plural, unless otherwise indicated herein or clearly contradicted by context.

As used herein, the term "and/or," in the context of selections such as "[A] and/or [B]," includes [A] alone, [B] alone, and both [A] and [B].

As used herein, the term "anti-tumor immune response" refers to a tumor-specific innate or adaptive immune response in the subject, such as, e.g., an increase in tumor-infiltrating immune cells, such as, e.g., tumor-infiltrating dendritic cells, tumor-infiltrating antigen presenting cells, tumor-infiltrating myeloid cells, tumor-infiltrating T-cells (such as, e.g., an increase in tumor-infiltrating CD4+ and CD8+ T cells, such as, e.g., an increase in activated cytotoxic effector CD4+ T cells); an increase in autoreactive T cells into the blood (i.e., an increase in recent thymic emigrants (RTE)). In some embodiments, the density of tumor-infiltrating T-cells in tumor tissues (number of cells by tumor surface area in mm$^2$) can be evaluated by immunohistochemistry and/or immunofluorescence studies. In some embodiments, RTE may be measured by multiparameter flow cytometric analysis of cluster of differentiation (CD)8+ and CD 4+ RTE.

As used herein, the term "tumor objective response" refers to a complete response or partial response to treatment as assessed using Response Evaluation Criteria In Solid Tumors Criteria (RECIST v1.1). RECIST response criteria for evaluation of target lesions include:

Complete Response (CR): Disappearance of all target lesions;

Partial Response (PR): At least 30% decrease in the sum of the longest diameter (LD) of target lesions;

Stable Disease (SD): Neither sufficient shrinkage to qualify for PR nor sufficient increase to qualify for progressive disease (PD), taking as reference the smallest sum LD since the treatment started;

Progressive disease (PD): At least a 20% increase in the sum of the LD of target lesions, taking as reference the smallest sum LD recorded since the treatment started or the appearance of one or more new lesions; Additionally, Overall Response Rate (ORR) is defined as (CR+ PR)/total number of subjects, and a "progression event" refers to a 20% increase in the sum of the longest diameter of target lesions, or a measurable increase in a non-target lesion, or the appearance of new lesions.

As used herein, the terms "comprising," "having," "including," and "containing" are to be construed as open-ended terms including the indicated component(s) but not excluding other elements (i.e., meaning "including, but not limited to") unless otherwise noted. The disclosure contemplates embodiments described as "comprising" a feature to include embodiments which "consist of" or "consist essentially of" the feature.

As used herein, the term "about," when used in connection with a dose or amount, include the value of a specified dose or amount or a range encompassing the dose or amount that is recognized by one of ordinary skill in the art to provide an effect equivalent to that obtained from the specified dose or amount. In some embodiments, the term "about" reflects a variation of 10% of a stated value. In some embodiments, the term "about" reflects a variation of 5% of a stated value. In some embodiments, the term "about" reflects a variation of 2% of a stated value. In some embodiments, the term "about" reflects a variation of 1% of a stated value. Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein. In any of the ranges described herein, the endpoints of the range are included in the range. However, the description also contemplates the same ranges in which the lower and/or the higher endpoint is excluded.

As used herein, the term "administer" and its cognates (e.g., "administering") includes both self-administration and administration to the patient by another person (e.g., a medical professional or caretaker).

As used herein, the term "co-administer" and its cognates (e.g., "co-administering") means administration of two or more therapeutic agents in a coordinated fashion and includes, but is not limited to, concurrent administration. Specifically, "co-administration" encompasses administration of a co-formulation or simultaneous administration of separate therapeutic compositions, as well as serial or sequential administration, provided that administration of one therapeutic agent is conditioned in some way on administration of another therapeutic agent. Illustratively, one therapeutic agent may be administered only after a different therapeutic agent has been administered and allowed to act for a prescribed period of time. Additionally, in some embodiments, co-administered therapeutic agents are present in the subject (PK), or otherwise induce an effect (PD), at similar, identical, or partially overlapping periods of time.

As used herein, the term "concomitant dose" refers to a dose of one therapeutic agent administered within about 24 hours (e.g., within about ±30 minutes, about ±1 hour, etc.) of the administration of another therapeutic agent.

As used herein, the term "antibody" refers to a protein having a conventional immunoglobulin format, comprising heavy and light chains, and comprising variable and constant regions. As a non-limiting example, an antibody may be an IgG which is a "Y-shaped" structure of two identical pairs of polypeptide chains, each pair having one "light" (e.g., having a molecular weight of about 25 kDa) and one "heavy" chain (e.g., having a molecular weight of about 50-70 kDa). As used herein, an "antibody" has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. The constant region allows the antibody to recruit cells and molecules of the immune system. The variable region is made of the N-terminal regions of each light chain and heavy chain, while the constant region is made of the C-terminal portions of each of the heavy and light chains. (Janeway et al., "Structure of the Antibody Molecule and the Immunoglobulin Genes", Immunobiology: The Immune System in Health and Disease, 4$^{th}$ ed. Elsevier Science Ltd./Garland Publishing, (1999)).

The general structure and properties of CDRs of antibodies have been described in the art. Briefly, in an antibody scaffold, the CDRs are embedded within a framework in the heavy and light chain variable region where they constitute the regions largely responsible for antigen binding and recognition. A variable region typically comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342:877-883), within a framework region (designated framework regions 1-4, FR1, FR2, FR3, and FR4, by Kabat et al., 1991; see also Chothia and Lesk, 1987, supra).

Antibodies can comprise any constant region known in the art. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the present disclosure include all such classes or isotypes of antibodies.

The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in some embodiments, the antibody is an antibody of isotype IgA, IgD, IgE, IgG, or IgM, including any one of IgG1, IgG2, IgG3 or IgG4.

As used herein, the term "chimeric antibody" refers to an antibody containing domains from two or more different antibodies. A chimeric antibody can, for example, contain the constant domains from one species and the variable domains from a second, or more generally, can contain stretches of amino acid sequence from at least two species. A chimeric antibody also may contain domains of two or more different antibodies within the same species.

As used herein, the term "humanized," when used in relation to an antibody, refers to an antibody having at least CDR regions from a non-human source which are engineered to have a structure and immunological function more similar to true human antibodies than the original source antibodies. As a non-limiting example, humanizing can involve grafting a CDR from a non-human antibody, such as, e.g., a mouse antibody, into a human antibody. Humanizing also can involve select amino acid substitutions to make a non-human sequence more similar to a human sequence.

As used herein, the term "conservative amino acid substitution" refers to the substitution of one amino acid with another amino acid having similar properties, e.g., size, charge, hydrophobicity, hydrophilicity, and/or aromaticity, and includes exchanges within one of the following five groups:

I. Small aliphatic, nonpolar or slightly polar residues: Ala, Ser, Thr, Pro, Gly;
  II. Polar, negatively charged residues and their amides and esters: Asp, Asn, Glu, Gln, cysteic acid and homocysteic acid;
  III. Polar, positively charged residues: His, Arg, Lys; Ornithine (Orn)
  IV. Large, aliphatic, nonpolar residues: Met, Leu, Ile, Val, Cys, Norleucine (Nle), homocysteine
  V. Large, aromatic residues: Phe, Tyr, Trp, acetyl phenylalanine.

As used herein, the terms "at [X] days(s)" and "at [Y] weeks(s)" and the like (e.g., day [X], week [Y]) refer to a specified time point, measured relative to a first dose or loading dose on day 1 (e.g., relative to a first loading dose of denosumab on day 1).

The terms "at least one" and "one or more" are used interchangeably herein and include one of an indicated component(s) and more than one (e.g., two, three, four, etc.) of an indicated component(s).

As used herein, the term "baseline sample," as in a "baseline tumor tissue sample" or a "baseline peripheral blood sample," refers to a biological sample, such as a tumor tissue sample or a peripheral blood sample, collected from the subject prior to the administration of the first dose of denosumab.

As used herein, the term "denosumab in an amount equivalent to [dose X] denosumab administered [on schedule Y]" and the like refer to a dosing regimen (i.e., a dose A of denosumab administered on a schedule B) that produces a pharmacokinetic profile in a subject that is substantially similar in one or more features (e.g., a mean serum concentration; a mean plasma area under the curve ($AUC_{0-\infty}$); a difference between the mean plasma $C_{max}$ at steady state and a mean plasma $C_{min}$ at steady state; a mean plasma $C_{max}$ at steady state) to a pharmacokinetic profile in a subject administered [dose X] denosumab [on schedule Y].

The terms "denosumab administration" and "denosumab treatment," when used in connection with a time period, refer to a time period in which a subject is administered denosumab according to a specific schedule (i.e., from the first dose to the end of the final cycle).

As used herein, the term "effective amount" or "therapeutically effective amount" refers to an amount of a therapeutic agent effective to treat a disease or disorder in a subject. In some embodiments, an effective amount refers to an amount effective, at dosages and for periods of time necessary, to achieve a desired therapeutic or prophylactic result, such as, e.g., an anti-tumor response.

As used herein, the term "loading dose" refers to a dose of a therapeutic agent administered, either as a single dose or as part of a series of doses, at the beginning of a course of treatment to initially induce a desired pharmacokinetic or pharmacodynamic effect. In some embodiments, the dose of and/or the dosing frequency for the loading dose(s) differ from the dosing regimen used later in the course of treatment to maintain or continue a desired pharmacokinetic or pharmacodynamic effect.

As used herein, the term "PD-1 inhibitor" refers to a therapeutic agent (such as, e.g., an antibody or small molecule therapeutic) that blocks the binding of PD-L1 to PD-1. In some embodiments, a PD-1 inhibitor may be an anti-PD-1 agent or an anti-PD-L1 agent, so long as the agent blocks the binding of PD-L1 to PD-1. In some embodiments, the PD-1 inhibitor is chosen from pembrolizumab, nivolumab, cemiplimab, dostarlimab, atezolizumab, avelumab, and durvalumab. In some embodiments, the PD-1 inhibitor is chosen from pembrolizumab and nivolumab. In some embodiments, the PD-1 inhibitor is pembrolizumab. In some embodiments, the PD-1 inhibitor is nivolumab. The term "PD-1 inhibitor" used herein is interchangeable with the term "PD-L1 inhibitor," unless context clearly indicates otherwise; "PD-1 inhibitor" may be replaced with "PD-L1 inhibitor" in all embodiments of the disclosure unless context clearly indicates otherwise.

As used herein, the term "pharmaceutically acceptable carrier" includes any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). Depending on the route of administration, a therapeutic agent may be coated in a material to protect it from the action of acids and other natural conditions that may inactivate the therapeutic agent.

As used herein, the term "progression event" refers to a 20% increase in the sum of the longest diameter of target lesions, or a measurable increase in a non-target lesion, or the appearance of new lesions.

As used herein, the terms "subject" and "patient" are used interchangeably and refer to an animal, e.g., a human. In some embodiments, the "subject" or "patient" is a human.

As used herein, the term "substantially similar," used in connection with a specific property, includes the specific property and properties recognized by one of ordinary skill in the art as providing an equivalent effect to the specific property. In some embodiments, when used in connection with a quantitative property, the term "substantially similar"

reflects a variation of 10% of the numerical value(s) corresponding to the quantitative property. In some embodiments, when used in connection with a quantitative property, the term "substantially similar" reflects a variation of 5% of the numerical value(s) corresponding to the quantitative property. In some embodiments, when used in connection with a quantitative property, the term "substantially similar" reflects a variation of 2% of the numerical value(s) corresponding to the quantitative property. In some embodiments, when used in connection with a quantitative property, the term "substantially similar" reflects a variation of 1% of numerical value(s) corresponding to the quantitative property.

As used herein, the term "treatment" and its cognates (e.g., "treat" or "treating") refer to improving at least one sign or symptom of a disease in a subject, delaying the onset of at least one sign or symptom of a disease in a subject, or lessening the severity of at least one sign or symptom of a disease. "Treatment" and its cognates do not necessarily imply 100% or complete treatment. Rather, there are varying degrees of treatment that one of ordinary skill in the art would recognize as having a potential benefit or therapeutic effect. Illustratively, in the context of treatment of melanoma, treatment may include, but is not limited to, an anti-tumor immune response, a Partial Response, a Complete Response, or disease stabilization.

As used herein, the term "treatment period" refers to a time period in which a subject is administered denosumab and/or another therapeutic agent according to a specific schedule (i.e., from the first dose to the end of the final dose cycle).

As used herein, the term "unit dose" refers to an amount of pharmaceutical composition, in particular the therapeutic agent therein (e.g., an anti-RANKL agent (e.g., denosumab), a PD-1 inhibitor (e.g., nivolumab, pembrolizumab)) that is administered to a subject in one treatment session. A treatment session may be continuous, e.g., uninterrupted parenteral administration (e.g., subcutaneous or intravenous) of a single bolus for a duration of time (e.g., 1 hour, 2 hours). A treatment session can also be divided into two or more subsessions, such that one unit dose is administered over time (e.g., 12 hours, 24 hours) with each bolus followed by a break or recovery time.

Agents Targeting RANK-L

Alternative aspects of the disclosure employ at least one agent targeting RANK-L in place of denosumab in a method, use, or pharmaceutical composition for use described herein. Agents targeting RANK-L include RANK-L antigen binding proteins (such as, e.g., anti-RANK-L antibodies, antigen binding fragments thereof, and anti-RANK-L antibody protein products, some of which are described in International Patent Application Publication Nos. WO 2018/200918 and WO 03/002713 and U.S. Pat. No. 7,364,736, each of which is incorporated herein by reference in its entirety). In some alternative embodiments, a RANK-L antigen binding protein that binds to human RANK-L, which has the amino acid sequence described in National Center for Biotechnology Information (NCBI) Reference Sequence No. NP003692, or SEQ ID NO: 1, and is encoded by the polynucleotide sequence of SEQ ID NO: 2, is employed in place of denosumab in a method, use, or pharmaceutical composition for use described herein.

TABLE 1

| Human RANKL Amino Acid and Nucleotide Sequences |
| --- |

| SEQ ID NO: | Description | Sequence |
| --- | --- | --- |
| 1 | Human RANKL (membrane bound) AA sequence | MRRASRDYTKYLRGSEEMGGGPGAPHEGPLHAPPPPAPHQPP AASRSMFVALLGLGLGQVVCSVALFFYFRAQMDPNRISEDGT HCIYRILRLHENADFQDTTLESQDTKLIPDSCRRIKQAFQGAV QKELQHIVGSQHIRAEKAMVDGSWLDLAKRSKLEAQPFAHL TINATDIPSGSHKVSLSSWYHDRGWAKISNMTFSNGKLIVNQ DGFYYLYANICFRHHETSGDLATEYLQLMVYVTKTSIKIPSSH TLMKGGSTKYWSGNSEFHFYSINVGGFFKLRSGEEISIEVSNPS LLDPDQDATYFGAFKVRDID |
| 2 | Human RANKL (membrane bound) nucleotide sequence | GCCCGCTCGCCCGCGCGCCCCAGGACCCAAAGCCGGGCTC CAAGTCGGCGCCCCACGTCGAGGCTCCGCCGCAGCCTCCG GAGTTGGCCGCAGACAAGAAGGGGAGGGAGCGGGAGAGG GAGGAGAGCTCCGAAGCGAGAGGGCCGAGCGCCATGCGC CGCGCCAGCAGAGACTACACCAAGTACCTGCGTGGCTCGG AGGAGATGGGCGGCGGCCCCGGAGCCCCGCACGAGGGCCC CCTGCACGCCCCGCCGCCGCCTGCGCCGCACCAGCCCCCTG CCGCCTCCCGCTCCATGTTCGTGGCCCTCCTGGGGCTGGGG CTGGGCCAGGTTGTCTGCAGCGTCGCCCTGTTCTTCTATTTC AGAGCGCAGATGGATCCTAATAGAATATCAGAAGATGGCA CTCACTGCATTTATAGAATTTTGAGACTCCATGAAAATGCA GATTTTCAAGCACAACTCTGGAGAGTCAAGATACAAAAT TAATACCTGATTCATGTAGGAGAATTAAACAGGCCTTTCAA GGAGCTGTGCAAAAGGAATTACAACATATCGTTGGATCAC AGCACATCAGAGCAGAGAAAGCGATGGTGGATGGCTCATG GTTAGATCTGGCCAAGAGGAGCAAGCTTGAAGCTCAGCCT TTTGCTCATCTCACTATTAATGCCACCGACATCCCATCTGG TTCCCATAAAGTGAGTCTGTCCTCTTGGTACCATGATCGGG GTTGGGCCAAGATCTCCAACATGACTTTTAGCAATGGAAA ACTAATAGTTAATCAGGATGGCTTTTATTACCTGTATGCCA ACATTTGCTTTCGACATCATGAAACTTCAGGAGACCTAGCT ACAGAGTATCTTCAACTAATGGTGTACGTCACTAAAACCA GCATCAAAATCCCAAGTTCTCATACCCTGATGAAAGGAGG AAGCACCAAGTATTGGTCAGGGAATTCTGAATTCCATTTTT ATTCCATAAACGTTGGTGGATTTTTTAAGTTACGGTCTGGA GAGGAAATCAGCATCGAGGTCTCCAACCCCTCCTTACTGG ATCCGGATCAGGATGCAACATACTTTGGGGCTTTTAAAGTT CGAGATATAGATTGAGCCCCAGTTTTTGGAGTGTTATGTAT TTCCTGGATGTTTGGAAACATTTTTTAAAACAAGCCAAGAA AGATGTATATAGGTGTGTGAGACTACTAAGAGGCATGGCC CCAACGGTACACGACTCAGTATCCATGCTCTTGACCTTGTA GAGAACACGCGTATTTACAGCCAGTGGGAGATGTTAGACT CATGGTGTGTTACACAATGGTTTTTAAATTTTGTAATGAAT TCCTAGAATTAAACCAGATTGGAGCAATTACGGGGTGACC TTATGAGAAACTGCATGTGGGCTATGGGAGGGGTTGGTCC CTGGTCATGTGCCCCTTCGCAGCTGAAGTGGAGAGGGTGTC ATCTAGCGCAATTGAAGGATCATCTGAAGGGGCAAATTCT TTTGAATTGTTACATCATGCTGGAACCTGCAAAAAATACTT TTTCTAATGAGGAGAGAAAATATATGTATTTTTATATAATA TCTAAAGTTATATTTCAGATGTAATGTTTTCTTTGCAAAGT ATTGTAAATTATATTTGTGCTATAGTATTTGATTCAAAATA TTTAAAAATGTCTTGCTGTTGACATATTTAATGTTTTAAATG TACAGACATATTTAACTGGTGCACTTTGTAAATTCCCTGGG GAAAACTTGCAGCTAAGGAGGGGAAAAAAATGTTGTTTCC TAATATCAAATGCAGTATATTTCTTCGTTCTTTTTAAGTTAA TAGATTTTTTCAGACTTGTCAAGCCTGTGCAAAAAAATTAA AATGGATGCCTTGAATAATAAGCAGGATGTTGGCCACCAG GTGCCTTTCAAATTTAGAAACTAATTGACTTTAGAAAGCTG ACATTGCCAAAAAGGATACATAATGGGCCACTGAAATCTG TCAAGAGTAGTTATATAATTGTTGAACAGGTGTTTTTCCAC AAGTGCCGCAAATTGTACCTTTTTTGTTTTTTTCAAAATAGA AAAGTTATTAGTGGTTTATCAGCAAAAAAGTCCAATTTTAA TTTAGTAAATGTTATCTTATACTGTACAATAAAAACATTGC CTTTGAATGTTAATTTTTTGGTACAAAAATAAATTTATATG AAAACCTGC |

In some embodiments, the RANK-L antigen binding protein is an anti-RANK-L antibody, or an antibody binding fragment thereof, or an anti-RANK-L antibody protein product.

In some embodiments, the anti-RANK-L antibody is a monoclonal antibody. Accordingly, in some embodiments, the present disclosure provides a liquid composition comprising a monoclonal antibody. Alternatively, in some embodiments, the liquid composition may be a polyclonal antibody composition. In some embodiments, the antibody comprises a sequence that is substantially similar to a naturally-occurring antibody produced by a mammal, e.g., mouse, rabbit, goat, horse, chicken, hamster, human, and the like. In this regard, the antibody can be considered as a mammalian antibody, e.g., a mouse antibody, rabbit antibody, goat antibody, horse antibody, chicken antibody, hamster antibody, human antibody, and the like. In some embodiments, the antibody is a human antibody. In some embodiments, the antibody is a chimeric antibody or a humanized antibody.

In some embodiments, the antibody is an anti-RANK-L antibody, such as, e.g., an anti-RANK-L monoclonal antibody. In some embodiments, the anti-RANK-L antibody is an IgG2 antibody. In some embodiments, the anti-RANK-L antibody binds to human RANK-L, which, in some embodiments, comprises the amino acid sequence of SEQ ID NO: 1 and is encoded by the nucleotide sequence of SEQ ID NO: 2.

In some embodiments, the antibody is denosumab or a biosimilar thereof. Denosumab is known in the art. See, e.g., International Nonproprietary Names for Pharmaceutical Substances (INN): Proposed INN: List 56, WHO Drug Information 20(3): 211 (2006); CAS Registry Number 615258-40-7. Denosumab is an immunoglobulin G2 (IgG2), also known as AMG 162, and is the active pharmaceutical ingredient of Prolia® and Xgeva®.

In some embodiments, the antibody comprises a light chain comprising a CDR1, CDR2, and CDR3 as set forth in Table 2. In some embodiments, the antibody comprises a heavy chain comprising a CDR1, CDR2, and CDR3 as set forth in Table 2. In some embodiments, the antibody comprises the VH and VL sequences recited in Table 2 or sequences comprising the VH-IgG2 and VL-IgG kappa sequences recited in Table 2. In some embodiments, the RANK-L antigen binding protein is an antibody comprising the amino acid sequences of SEQ ID NOs: 3-8. In some embodiments, the anti-RANK-L antibody comprises six CDR amino acid sequences of SEQ ID NOs: 3-8. In some embodiments, the anti-RANK-L antibody comprises a heavy chain (HC) complementarity-determining region (CDR) 1 amino acid sequence of SEQ ID NO: 3, an HC CDR2 amino acid sequence of SEQ ID NO: 4, an HC CDR3 amino acid sequence of SEQ ID NO: 5, a light chain (LC) CDR1 amino acid sequence of SEQ ID NO: 6, an LC CDR2 amino acid sequence of SEQ ID NO: 7, and an LC CDR3 amino acid sequence of SEQ ID NO: 8. In some embodiments, the anti-RANK-L antibody comprises a RANK-L-binding domain comprising (a) a heavy chain variable region (VH) that comprises: (i) a VH complementarity determining region one (CDR-H1) comprising the amino acid sequence of SEQ ID NO: 3; (ii) a CDR-H2 comprising the amino acid sequence of SEQ ID NO: 4; and (iii) a CDR-H3 comprising the amino acid sequence of SEQ ID NO: 5; and (b) a light chain variable region (VL) that comprises: (i) a VL complementarity determining region one (CDR-L1) comprising the amino acid sequence of SEQ ID NO: 6; (ii) a CDR-L2 comprising the amino acid sequence of SEQ ID NO: 7; and (iii) a CDR-L3 comprising the amino acid sequence of SEQ ID NO: 8. In some embodiments, the RANK-L-binding domain comprises: a VH that comprises the amino acid sequence of SEQ ID NO: 9, and a VL that comprises the amino acid sequence of SEQ ID NO: 10. In some embodiments, the anti-RANK-L antibody comprises a VH comprising the amino acid sequence of SEQ ID NO: 9 and a VL comprising the amino acid sequence of SEQ ID NO: 10. In some embodiments, the anti-RANK-L antibody comprises a HC comprising the amino acid sequence of SEQ ID NO: 11 or 13 and a LC comprising the amino acid sequence of SEQ ID NO: 12.

TABLE 2

| Denosumab Amino Acid Sequences | | |
|---|---|---|
| Description | Sequence | SEQ ID NO: |
| HC CDR1 | SYAMS | 3 |
| HC CDR2 | GITGSGGSTYYADSVK | 4 |
| HC CDR3 | DPGTTVIMSWFDP | 5 |
| LC CDR1 | RASQSVRGRYLA | 6 |
| LC CDR2 | GASSRAT | 7 |
| LC CDR3 | QQYGSSPRT | 8 |
| VH | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSS | 9 |
| VL | EIVLTQSPGTLSLSPGERATLSCRASQSVRGRYLAWYQQ KPGQAPRLLIYGASSRATGIPDRFSGSGSGTDFTLTISRLE PEDFAVFYCQQYGSSPRTFGQGTKVEIK | 10 |
| VH-IgG2 | EVQLLESGGGLVQPGGSLRLSCAASGFTFSSYAMSWVR QAPGKGLEWVSGITGSGGSTYYADSVKGRFTISRDNSK NTLYLQMNSLRAEDTAVYYCAKDPGTTVIMSWFDPWG QGTLVTVSSASTKGPSVFPLAPCSRSTSESTAALGCLVK DYFPEPVTVSWNSGALTSGVHTFPAVLQSSGLYSLSSVV TVPSSNFGTQTYTCNVDHKPSNTKVDKTVERKCCVECP PCPAPPVAGPSVFLFPPKPKDTLMISRTPEVTCVVVDVS HEDPEVQFNWYVDGVEVHNAKTKPREEQFNSTFRVVS VLTVVHQDWLNGKEYKCKVSNKGLPAPIEKTISKTKGQ PREPQVYTLPPSREEMTKNQVSLTCLVKGFYPSDIAVEW ESNGQPENNYKTTPPMLDSDGSFFLYSKLTVDKSRWQQ GNVFSCSVMHEALHNHYTQKSLSLSP (GK) * | 11 |

TABLE 2-continued

Denosumab Amino Acid Sequences

| Description | Sequence | SEQ ID NO: |
|---|---|---|
| VL-IgG Kappa | EIVLTQSPGTLSLSPGERATLSCRASQSVRGRYLAWYQQ KPGQAPRLLIYGASSRATGIPDRFSGSGSGTDFTLTISRLE PEDFAVFYCQQYGSSPRTFGQGTKVEIKRTVAAPSVFIFP PSDEQLKSGTASVVCLLNNFYPREAKVQWKVDNALQS GNSQESVTEQDSKDSTYSLSSTLTLSKADYEKHKVYAC EVTHQGLSSPVTKSFNRGEC | 12 |

LC, light chain; HC, heavy chain; VL, variable light chain; VH, variable heavy chain.
*Terminal residues G and K may be clipped during recombinant production process.

In some embodiments, the antibody comprises:
  i. a heavy chain (HC) CDR1 comprising an amino acid sequence of SEQ ID NO: 3 or an amino acid sequence which is at least 90% (e.g., at least 95%, at least 96%, at least 97%, at least 98%, or at least 99%) identical to SEQ ID NO: 3 or a variant amino acid sequence of SEQ ID NO: 3 with 1 or 2 amino acid substitutions;
  ii. a HC CDR2 comprising an amino acid sequence of SEQ ID NO: 4 or an amino acid sequence which is at least 90% (e.g., at least 95%, at least 96%, at least 97%, at least 98%, or at least 99%) identical to SEQ ID NO: 4 or a variant amino acid sequence of SEQ ID NO: 4 with 1 or 2 amino acid substitutions;
  iii. a HC CDR3 comprising an amino acid sequence of SEQ ID NO: 5 or an amino acid sequence which is at least 90% (e.g., at least 95%, at least 96%, at least 97%, at least 98%, or at least 99%) identical to SEQ ID NO: 5 or a variant amino acid sequence of SEQ ID NO: 5 with 1 or 2 amino acid substitutions.
  iv. a light chain (LC) CDR1 comprising an amino acid sequence of SEQ ID NO: 6 or an amino acid sequence which is at least 90% (e.g., at least 95%, at least 96%, at least 97%, at least 98% or at least 99%) identical to SEQ ID NO: 6 or a variant amino acid sequence of SEQ ID NO: 6 with 1 or 2 amino acid substitutions,
  v. a LC CDR2 comprising an amino acid sequence of SEQ ID NO: 7 or an amino acid sequence which is at least 90% (e.g., at least 95%, at least 96%, at least 97%, at least 98%, or at least 99%) identical to SEQ ID NO: 7 or a variant amino acid sequence of SEQ ID NO: 7 with 1 or 2 amino acid substitutions,
  vi. a LC CDR3 comprising an amino acid sequence of SEQ ID NO: 8 or an amino acid sequence which is at least 90% (e.g., at least 95%, at least 96%, at least 97%, at least 98%, or at least 99%) identical to SEQ ID NO: 8 or a variant amino acid sequence of SEQ ID NO: 8 with 1 or 2 amino acid substitutions.

In some embodiments, the antibody comprises: a HC variable region comprising an amino acid sequence of SEQ ID NO: 9, an amino acid sequence which is at least 90% (e.g., at least 95%, at least 96%, at least 97%, at least 98%, or at least 99%) identical to SEQ ID NO: 9, or a variant amino acid sequence of SEQ ID NO: 9 with 1 to 10 (e.g., 1 to 9, 1 to 8, 1 to 7, 1 to 6, 1 to 5, 1 to 4, 1 to 3, 1 or 2) amino acid substitutions.

In some embodiments, the antibody comprises: a LC variable region comprising an amino acid sequence of SEQ ID NO: 10, an amino acid sequence which is at least 90% (e.g., at least 95%, at least 96%, at least 97%, at least 98%, or at least 99%) identical to SEQ ID NO: 10, or a variant amino acid sequence of SEQ ID NO: 10 with 1 to 10 (e.g., 1 to 9, 1 to 8, 1 to 7, 1 to 6, 1 to 5, 1 to 4, 1 to 3, 1 or 2) amino acid substitutions.

In some embodiments, the antibody comprises a heavy chain comprising an amino acid sequence of SEQ ID NO: 11, an amino acid sequence which is at least 90% (e.g., at least 95%, at least 96%, at least 97%, at least 98%, or at least 99%) identical to SEQ ID NO: 11, or a variant amino acid sequence of SEQ ID NO: 11 with 1 to 10 (e.g., 1 to 9, 1 to 8, 1 to 7, 1 to 6, 1 to 5, 1 to 4, 1 to 3, 1 or 2) amino acid substitutions.

In some embodiments, the terminal lysine may be absent. In some embodiments, the terminal lysine may be present. In some embodiments, the terminal glycine-lysine may be absent. In some embodiments, the terminal glycine-lysine may be present. C-terminal lysine clipping is a common phenomenon occurring during the bioproduction of monoclonal antibodies. Often, the lysine residue is removed via carboxypeptidase D (CpD), which results in generation of a mixture of antibody isoforms bearing zero or one C-terminal lysine residues on each heavy chain. Further, following C-terminal lysine cleavage, peptidylglycine α-amidating monooxygenase (PAM) catalyzes the hydroxylation of glycine and removal of the glyoxylate from the glycine residue, leaving an amidated C-terminal proline. Therefore, during recombinant production of a monoclonal antibody, the product is often a mixture of C-terminal processing variants, with heavy chain C-terminus ends at (amidated) proline, glycine, or lysine.

In some embodiments, the antibody comprises a light chain comprising an amino acid sequence of SEQ ID NO: 12, an amino acid sequence which is at least 90% (e.g., at least 95%, at least 96%, at least 97%, at least 98%, or at least 99%) identical to SEQ ID NO: 12, or a variant amino acid sequence of SEQ ID NO: 12 with 1 to 10 (e.g., 1 to 9, 1 to 8, 1 to 7, 1 to 6, 1 to 5, 1 to 4, 1 to 3, 1 or 2) amino acid substitutions.

In some embodiments, the amino acid substitution is a conservative amino acid substitution.

In alternative embodiments of the disclosure, a biosimilar of denosumab may be used in place of denosumab in a method, use, or pharmaceutical composition described herein.

PD-1 Inhibitors

In some embodiments of the present disclosure, a PD-1 inhibitor is co-administered with at least one agent targeting RANK-L (e.g., denosumab). In some embodiments, the PD-1 inhibitor is an anti-PD-1 or anti-PD-L1 antibody, or an antibody binding fragment thereof, or an anti-PD-1 or anti-PD-L1 antibody protein product.

In some embodiments, the PD-1 inhibitor is a monoclonal antibody. Accordingly, in some embodiments, the present disclosure provides a liquid composition comprising a monoclonal antibody. Alternatively, in some embodiments, the liquid composition may be a polyclonal antibody composition. In some embodiments, the antibody comprises a sequence that is substantially similar to a naturally-occurring antibody produced by a mammal, e.g., mouse, rabbit, goat, horse, chicken, hamster, human, and the like. In this regard, the antibody can be considered as a mammalian antibody, e.g., a mouse antibody, rabbit antibody, goat antibody, horse antibody, chicken antibody, hamster antibody, human antibody, and the like. In some embodiments, the antibody is a human antibody. In some embodiments, the antibody is a chimeric antibody or a humanized antibody.

In some embodiments, the antibody is an anti-PD-1 or anti-PD-L1 antibody, such as, e.g., an anti-PD-1 or anti-PD-L1 monoclonal antibody.

In some embodiments, the antibody is chosen from pembrolizumab, nivolumab, cemiplimab, dostarlimab, atezolizumab, avelumab, durvalumab, and biosimilars of any of the foregoing. In some embodiments, the PD-1 inhibitor is chosen from pembrolizumab, nivolumab, and biosimilars of any of the foregoing. In some embodiments, the PD-1 inhibitor is pembrolizumab or a biosimilar thereof. In some embodiments, the PD-1 inhibitor is nivolumab of a biosimilar thereof.

In some embodiments, the PD-1 inhibitor is an antibody comprising a light chain comprising a CDR1, CDR2, and CDR3 as set forth in Table 3. In some embodiments, the PD-1 inhibitor is an antibody comprising a heavy chain comprising a CDR1, CDR2, and CDR3 as set forth in Table 3. In some embodiments, the PD-1 inhibitor is an antibody comprising the VH and VL sequences recited in Table 3. In some embodiments, the PD-1 inhibitor is an antibody comprising the amino acid sequences of SEQ ID NOs: 13-18. In some embodiments, the PD-1 inhibitor comprises six CDR amino acid sequences of SEQ ID NOs: 13-18. In some embodiments, the PD-1 inhibitor comprises a heavy chain (HC) complementarity-determining region (CDR) 1 amino acid sequence of SEQ ID NO: 13, an HC CDR2 amino acid sequence of SEQ ID NO: 14, an HC CDR3 amino acid sequence of SEQ ID NO: 15, a light chain (LC) CDR1 amino acid sequence of SEQ ID NO: 16, an LC CDR2 amino acid sequence of SEQ ID NO: 17, and an LC CDR3 amino acid sequence of SEQ ID NO: 18. In some embodiments, the PD-1 inhibitor comprises a PD-1 binding domain comprising (a) a heavy chain variable region (VH) that comprises: (i) a VH complementarity determining region one (CDR-H1) comprising the amino acid sequence of SEQ ID NO: 13; (ii) a CDR-H2 comprising the amino acid sequence of SEQ ID NO: 14; and (iii) a CDR-H3 comprising the amino acid sequence of SEQ ID NO: 15; and (b) a light chain variable region (VL) that comprises: (i) a VL complementarity determining region one (CDR-L1) comprising the amino acid sequence of SEQ ID NO: 16; (ii) a CDR-L2 comprising the amino acid sequence of SEQ ID NO: 17; and (iii) a CDR-L3 comprising the amino acid sequence of SEQ ID NO: 18. In some embodiments, the PD-1 binding domain comprises: a VH that comprises the amino acid sequence of SEQ ID NO: 19, and a VL that comprises the amino acid sequence of SEQ ID NO: 20. In some embodiments, the PD-1 inhibitor comprises a VH comprising the amino acid sequence of SEQ ID NO: 19 and a VL comprising the amino acid sequence of SEQ ID NO: 20. In some embodiments, the PD-1 inhibitor comprises a HC comprising the amino acid sequence of SEQ ID NO: 21 and a LC comprising the amino acid sequence of SEQ ID NO: 22.

TABLE 3

| Nivolumab Amino Acid Sequences | | |
| --- | --- | --- |
| Description | Sequence | SEQ ID NO: |
| HC CDR1 | NSGMH | 13 |
| HC CDR2 | VIWYDGSKRYYADSVKG | 14 |
| HC CDR3 | NDDY | 15 |
| LC CDR1 | RASQSVSSYLA | 16 |
| LC CDR2 | DASNRAT | 17 |
| LC CDR3 | QQSSNWPRT | 18 |
| VH | QVQLVESGGGVVQPGRSLRLDCKASGITFSNSGMHWV RQAPGKGLEWVAVIWYDGSKRYYADSVKGRFTISRDN SKNTLFLQMNSLRAEDTAVYYCATNDDYWGQGTLVTV SS | 19 |
| VL | EIVLTQSPATLSLSPGERATLSCRASQSVSSYLAWYQQK PGQAPRLLIYDASNRATGIPARFSGSGSGTDFTLTISSLEP EDFAVYYCQQSSNWPRTFGQGTKVEIK | 20 |
| HC | QVQLVESGGGVVQPGRSLRLDCKASGITFSNSGMHWV RQAPGKGLEWVAVIWYDGSKRYYADSVKGRFTISRDN SKNTLFLQMNSLRAEDTAVYYCATNDDYWGQGTLVTV SSASTKGPSVFPLAPCSRSTSESTAALGCLVKDYFPEPVT VSWNSGALTSGVHTFPAVLQSSGLYSLSSVVTVPSSSLG TKTYTCNVDHKPSNTKVDKRVESKYGPPCPPCPAPEFL GGPSVFLFPPKPKDTLMISRTPEVTCVVVDVSQEDPEVQ FNWYVDGVEVHNAKTKPREEQFNSTYRVVSVLTVLHQ DWLNGKEYKCKVSNKGLPSSIEKTISKAKGQPREPQVY TLPPSQEEMTKNQVSLTCLVKGFYPSDIAVEWESNGQPE NNYKTTPPVLDSDGSFFLYSRLTVDKSRWQEGNVFSCS VMHEALHNHYTQKSLSLSLGK | 21 |

TABLE 3-continued

Nivolumab Amino Acid Sequences

| Description | Sequence | SEQ ID NO: |
|---|---|---|
| LC | EIVLTQSPATLSLSPGERATLSCRASQSVSSYLAWYQQK PGQAPRLLIYDASNRATGIPARFSGSGSGTDFTLTISSLEP EDFAVYYCQQSSNWPRTFGQGTKVEIKRTVAAPSVFIFP PSDEQLKSGTASVVCLLNNFYPREAKVQWKVDNALQS GNSQESVTEQDSKDSTYSLSSTLTLSKADYEKHKVYAC EVTHQGLSSPVTKSFNRGEC | 22 |

LC, light chain; HC, heavy chain; VL, variable light chain; VH, variable heavy chain.
*Terminal residues G and K may be clipped during recombinant production process.

In some embodiments, the PD-1 inhibitor comprises:

i. a heavy chain (HC) CDR1 comprising an amino acid sequence of SEQ ID NO: 13 or an amino acid sequence which is at least 90% (e.g., at least 95%, at least 96%, at least 97%, at least 98%, or at least 99%) identical to SEQ ID NO: 13 or a variant amino acid sequence of SEQ ID NO: 13 with 1 or 2 amino acid substitutions;

ii. a HC CDR2 comprising an amino acid sequence of SEQ ID NO: 14 or an amino acid sequence which is at least 90% (e.g., at least 95%, at least 96%, at least 97%, at least 98%, or at least 99%) identical to SEQ ID NO: 14 or a variant amino acid sequence of SEQ ID NO: 14 with 1 or 2 amino acid substitutions;

iii. a HC CDR3 comprising an amino acid sequence of SEQ ID NO: 15 or an amino acid sequence which is at least 90% (e.g., at least 95%, at least 96%, at least 97%, at least 98%, or at least 99%) identical to SEQ ID NO: 15 or a variant amino acid sequence of SEQ ID NO: 15 with 1 or 2 amino acid substitutions.

iv. a light chain (LC) CDR1 comprising an amino acid sequence of SEQ ID NO: 16 or an amino acid sequence which is at least 90% (e.g., at least 95%, at least 96%, at least 97%, at least 98% or at least 99%) identical to SEQ ID NO: 16 or a variant amino acid sequence of SEQ ID NO: 16 with 1 or 2 amino acid substitutions, v. a LC CDR2 comprising an amino acid sequence of SEQ ID NO: 17 or an amino acid sequence which is at least 90% (e.g., at least 95%, at least 96%, at least 97%, at least 98%, or at least 99%) identical to SEQ ID NO: 17 or a variant amino acid sequence of SEQ ID NO: 17 with 1 or 2 amino acid substitutions, vi. a LC CDR3 comprising an amino acid sequence of SEQ ID NO: 18 or an amino acid sequence which is at least 90% (e.g., at least 95%, at least 96%, at least 97%, at least 98%, or at least 99%) identical to SEQ ID NO: 18 or a variant amino acid sequence of SEQ ID NO: 18 with 1 or 2 amino acid substitutions.

In some embodiments, the PD-1 inhibitor comprises: a HC variable region comprising an amino acid sequence of SEQ ID NO: 19, an amino acid sequence which is at least 90% (e.g., at least 95%, at least 96%, at least 97%, at least 98%, or at least 99%) identical to SEQ ID NO: 19, or a variant amino acid sequence of SEQ ID NO: 19 with 1 to 10 (e.g., 1 to 9, 1 to 8, 1 to 7, 1 to 6, 1 to 5, 1 to 4, 1 to 3, 1 or 2) amino acid substitutions.

In some embodiments, the PD-1 inhibitor comprises: a LC variable region comprising an amino acid sequence of SEQ ID NO: 20, an amino acid sequence which is at least 90% (e.g., at least 95%, at least 96%, at least 97%, at least 98%, or at least 99%) identical to SEQ ID NO: 20, or a variant amino acid sequence of SEQ ID NO: 20 with 1 to 10

(e.g., 1 to 9, 1 to 8, 1 to 7, 1 to 6, 1 to 5, 1 to 4, 1 to 3, 1 or 2) amino acid substitutions.

In some embodiments, the PD-1 inhibitor comprises a heavy chain comprising an amino acid sequence of SEQ ID NO: 21, an amino acid sequence which is at least 90% (e.g., at least 95%, at least 96%, at least 97%, at least 98%, or at least 99%) identical to SEQ ID NO: 21, or a variant amino acid sequence of SEQ ID NO: 21 with 1 to 10 (e.g., 1 to 9, 1 to 8, 1 to 7, 1 to 6, 1 to 5, 1 to 4, 1 to 3, 1 or 2) amino acid substitutions.

In some embodiments, the PD-1 inhibitor comprises a light chain comprising an amino acid sequence of SEQ ID NO: 22, an amino acid sequence which is at least 90% (e.g., at least 95%, at least 96%, at least 97%, at least 98%, or at least 99%) identical to SEQ ID NO: 22, or a variant amino acid sequence of SEQ ID NO: 22 with 1 to 10 (e.g., 1 to 9, 1 to 8, 1 to 7, 1 to 6, 1 to 5, 1 to 4, 1 to 3, 1 or 2) amino acid substitutions.

In some embodiments, the amino acid substitution is a conservative amino acid substitution.

In some embodiments, the PD-1 inhibitor is an antibody comprising a light chain comprising a CDR1, CDR2, and CDR3 as set forth in Table 4. In some embodiments, the PD-1 inhibitor is an antibody comprising a heavy chain comprising a CDR1, CDR2, and CDR3 as set forth in Table 4. In some embodiments, the PD-1 inhibitor is an antibody comprising the VH and VL sequences recited in Table 4. In some embodiments, the PD-1 inhibitor is an antibody comprising the amino acid sequences of SEQ ID NOs: 23-28. In some embodiments, the PD-1 inhibitor comprises six CDR amino acid sequences of SEQ ID NOs: 23-28. In some embodiments, the PD-1 inhibitor comprises a heavy chain (HC) complementarity-determining region (CDR) 1 amino acid sequence of SEQ ID NO: 23, an HC CDR2 amino acid sequence of SEQ ID NO: 24, an HC CDR3 amino acid sequence of SEQ ID NO: 25, a light chain (LC) CDR1 amino acid sequence of SEQ ID NO: 26, an LC CDR2 amino acid sequence of SEQ ID NO: 27, and an LC CDR3 amino acid sequence of SEQ ID NO: 28. In some embodiments, the PD-1 inhibitor comprises a PD-1 binding domain comprising (a) a heavy chain variable region (VH) that comprises: (i) a VH complementarity determining region one (CDR-H1) comprising the amino acid sequence of SEQ ID NO: 23; (ii) a CDR-H2 comprising the amino acid sequence of SEQ ID NO: 24; and (iii) a CDR-H3 comprising the amino acid sequence of SEQ ID NO: 25; and (b) a light chain variable region (VL) that comprises: (i) a VL complementarity determining region one (CDR-L1) comprising the amino acid sequence of SEQ ID NO: 26; (ii) a CDR-L2 comprising the amino acid sequence of SEQ ID NO: 27; and (iii) a CDR-L3 comprising the amino acid sequence of SEQ ID NO: 28. In some embodiments, the PD-1 binding domain comprises: a VH that comprises the amino acid sequence of SEQ ID NO: 29, and a VL that comprises the amino acid sequence of SEQ ID NO: 30. In some embodiments, the PD-1 inhibitor comprises a VH comprising the amino acid sequence of SEQ ID NO: 29 and a VL comprising the amino acid sequence of SEQ ID NO: 30. In some embodiments, the PD-1 inhibitor comprises a HC comprising the amino acid sequence of SEQ ID NO: 31 and a LC comprising the amino acid sequence of SEQ ID NO: 32.

least 90% (e.g., at least 95%, at least 96%, at least 97%, at least 98%, or at least 99%) identical to SEQ ID NO: 25 or a variant amino acid sequence of SEQ ID NO: 25 with 1 or 2 amino acid substitutions.

iv. a light chain (LC) CDR1 comprising an amino acid sequence of SEQ ID NO: 26 or an amino acid sequence which is at least 90% (e.g., at least 95%, at least 96%, at least 97%, at least 98% or at least 99%) identical to SEQ ID NO: 26 or a variant amino acid sequence of SEQ ID NO: 26 with 1 or 2 amino acid substitutions,

TABLE 4

Pembrolizumab Amino Acid Sequences

| Description | Sequence | SEQ ID NO: |
|---|---|---|
| HC CDR1 | NYYMY | 23 |
| HC CDR2 | GINPSNGGTNFNEKFKN | 24 |
| HC CDR3 | RDYRFDMGFDY | 25 |
| LC CDR1 | RASKGVSTSGYSYLH | 26 |
| LC CDR2 | LASYLES | 27 |
| LC CDR3 | QHSRDLPLT | 28 |
| VH | QVQLVQSGVEVKKPGASVKVSCKASGYTFTNYYMYW VRQAPGQGLEWMGGINPSNGGTNFNEKFKNRVTLTTDS STTTAYMELKSLQFDDTAVYYCARRDYRFDMGFDYWG QGTTVTVSS | 29 |
| VL | EIVLTQSPATLSLSPGERATLSCRASKGVSTSGYSYLHW YQQKPGQAPRLLIYLASYLESGVPARFSGSGSGTDFTLTI SSLEPEDFAVYYCQHSRDLPLTFGGGTKVEIK | 30 |
| HC | QVQLVQSGVEVKKPGASVKVSCKASGYTFTNYYMYW VRQAPGQGLEWMGGINPSNGGTNFNEKFKNRVTLTTDS STTTAYMELKSLQFDDTAVYYCARRDYRFDMGFDYWG QGTTVTVSSASTKGPSVFPLAPCSRSTSESTAALGCLVK DYFPEPVTVSWNSGALTSGVHTFPAVLQSSGLYSLSSVV TVPSSSLGTKTYTCNVDHKPSNTKVDKRVESKYGPPCPP CPAPEFLGGPSVFLFPPKPKDTLMISRTPEVTCVVVDVS QEDPEVQFNWYVDGVEVHNAKTKPREEQFNSTYRVVS VLTVLHQDWLNGKEYKCKVSNKGLPSSIEKTISKAKGQ PREPQVYTLPPSQEEMTKNQVSLTCLVKGFYPSDIAVE WESNGQPENNYKTTPPVLDSDGSFFLYSRLTVDKSRWQ EGNVFSCSVMHEALHNHYTQKSLSLSLGK | 31 |
| LC | EIVLTQSPATLSLSPGERATLSCRASKGVSTSGYSYLHW YQQKPGQAPRLLIYLASYLESGVPARFSGSGSGTDFTLTI SSLEPEDFAVYYCQHSRDLPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC | 32 |

LC, light chain; HC, heavy chain; VL, variable light chain; VH, variable heavy chain.
*Terminal residues G and K may be clipped during recombinant production process.

In some embodiments, the PD-1 inhibitor comprises:

i. a heavy chain (HC) CDR1 comprising an amino acid sequence of SEQ ID NO: 23 or an amino acid sequence which is at least 90% (e.g., at least 95%, at least 96%, at least 97%, at least 98%, or at least 99%) identical to SEQ ID NO: 23 or a variant amino acid sequence of SEQ ID NO: 23 with 1 or 2 amino acid substitutions;

ii. a HC CDR2 comprising an amino acid sequence of SEQ ID NO: 24 or an amino acid sequence which is at least 90% (e.g., at least 95%, at least 96%, at least 97%, at least 98%, or at least 99%) identical to SEQ ID NO: 24 or a variant amino acid sequence of SEQ ID NO: 24 with 1 or 2 amino acid substitutions;

iii. a HC CDR3 comprising an amino acid sequence of SEQ ID NO: 25 or an amino acid sequence which is at v. a LC CDR2 comprising an amino acid sequence of SEQ ID NO: 27 or an amino acid sequence which is at least 90% (e.g., at least 95%, at least 96%, at least 97%, at least 98%, or at least 99%) identical to SEQ ID NO: 27 or a variant amino acid sequence of SEQ ID NO: 27 with 1 or 2 amino acid substitutions, vi. a LC CDR3 comprising an amino acid sequence of SEQ ID NO: 28 or an amino acid sequence which is at least 90% (e.g., at least 95%, at least 96%, at least 97%, at least 98%, or at least 99%) identical to SEQ ID NO: 28 or a variant amino acid sequence of SEQ ID NO: 28 with 1 or 2 amino acid substitutions.

In some embodiments, the PD-1 inhibitor comprises: a HC variable region comprising an amino acid sequence of SEQ ID NO: 29, an amino acid sequence which is at least 90% (e.g., at least 95%, at least 96%, at least 97%, at least 98%, or at least 99%) identical to SEQ ID NO: 29, or a variant amino acid sequence of SEQ ID NO: 29 with 1 to 10 (e.g., 1 to 9, 1 to 8, 1 to 7, 1 to 6, 1 to 5, 1 to 4, 1 to 3, 1 or 2) amino acid substitutions.

In some embodiments, the PD-1 inhibitor comprises: a LC variable region comprising an amino acid sequence of SEQ ID NO: 30, an amino acid sequence which is at least 90% (e.g., at least 95%, at least 96%, at least 97%, at least 98%, or at least 99%) identical to SEQ ID NO: 30, or a variant amino acid sequence of SEQ ID NO: 30 with 1 to 10 (e.g., 1 to 9, 1 to 8, 1 to 7, 1 to 6, 1 to 5, 1 to 4, 1 to 3, 1 or 2) amino acid substitutions.

In some embodiments, the PD-1 inhibitor comprises a heavy chain comprising an amino acid sequence of SEQ ID NO: 31, an amino acid sequence which is at least 90% (e.g., at least 95%, at least 96%, at least 97%, at least 98%, or at least 99%) identical to SEQ ID NO: 31, or a variant amino acid sequence of SEQ ID NO: 31 with 1 to 10 (e.g., 1 to 9, 1 to 8, 1 to 7, 1 to 6, 1 to 5, 1 to 4, 1 to 3, 1 or 2) amino acid substitutions.

In some embodiments, the PD-1 inhibitor comprises a light chain comprising an amino acid sequence of SEQ ID NO: 32, an amino acid sequence which is at least 90% (e.g., at least 95%, at least 96%, at least 97%, at least 98%, or at least 99%) identical to SEQ ID NO: 32, or a variant amino acid sequence of SEQ ID NO: 32 with 1 to 10 (e.g., 1 to 9, 1 to 8, 1 to 7, 1 to 6, 1 to 5, 1 to 4, 1 to 3, 1 or 2) amino acid substitutions.

In some embodiments, the amino acid substitution is a conservative amino acid substitution.

In alternative embodiments of the present disclosure, a biosimilar of pembrolizumab, nivolumab, cemiplimab, dostarlimab, atezolizumab, avelumab, and durvalumab may be used in place of pembrolizumab, nivolumab, cemiplimab, dostarlimab, atezolizumab, avelumab, and durvalumab, respectively, in a method, use, or pharmaceutical composition described herein.

Subjects

In some embodiments of the presently disclosed methods, the subject is a human subject. In some embodiments, the human subject is about 18 years old or older. In some embodiments, the human subject is about 30 years or older. In some embodiments, the human subject is about 60 years or older.

In some embodiments, a baseline tumor tissue sample from the subject comprises brisk tumor-infiltrating lymphocytes (TILs). In some embodiments, a baseline peripheral blood sample from the subject comprises high serum-free RANKL and/or low serum OPG levels as assessed by flow cytometric analysis. In some embodiments, a baseline tumor tissue sample from the subject expresses two or more of Sox10, RANK, and OPG as assessed by immunohistochemistry.

In some embodiments, the subject has not previously received a PD-1 inhibitor. In some embodiments, the subject previously received a PD-1 inhibitor in stage III or stage IV melanoma and the interval between the last dose of the PD-1 inhibitor and the date of relapse is at least about one year.

In some embodiments, the subject does not have bone metastases. In some embodiments, the subject does not have hypercalcemia.

In some embodiments, the subject meets at least one of the inclusion criteria of the clinical trial described in Example 1 of this application.

In some embodiments, the subject does not meet any of the exclusion criteria of the clinical trial described in Example 1 of this application.

Melanoma

Some embodiments of the present disclosure provide methods of treating melanoma in a subject in need thereof. In some embodiments, the melanoma is cutaneous melanoma or mucosal melanoma. In some embodiments, the melanoma is cutaneous melanoma. In some embodiments, the melanoma is mucosal melanoma.

In some embodiments, the melanoma is stage III melanoma or stage IV melanoma. In some embodiments, the melanoma is stage III cutaneous melanoma or stage IV cutaneous melanoma. In some embodiments, the melanoma is stage III mucosal melanoma or stage IV mucosal melanoma.

In some embodiments, the melanoma is stage III melanoma. In some embodiments, the melanoma is stage III cutaneous melanoma. In some embodiments, the melanoma is stage III mucosal melanoma.

In some embodiments, the melanoma is stage IV melanoma. In some embodiments, the melanoma is stage IV cutaneous melanoma. In some embodiments, the melanoma is stage IV mucosal melanoma.

In some embodiments, the melanoma is American Joint Committee on Cancer (AJCC) stage III melanoma or AJCC stage IV melanoma. In some embodiments, the melanoma is AJCC stage III cutaneous melanoma or AJCC stage IV cutaneous melanoma. In some embodiments, the melanoma is AJCC stage III mucosal melanoma or AJCC stage IV mucosal melanoma.

In some embodiments, the melanoma is AJCC stage III melanoma. In some embodiments, the melanoma is AJCC stage III cutaneous melanoma. In some embodiments, the melanoma is AJCC stage III mucosal melanoma.

In some embodiments, the melanoma is AJCC stage IV melanoma. In some embodiments, the melanoma is AJCC stage IV cutaneous melanoma. In some embodiments, the melanoma is AJCC stage IV mucosal melanoma.

In some embodiments, the melanoma is unresectable.

In some embodiments, the melanoma is resectable stage III melanoma.

Routes of Administration and Pharmaceutical Compositions

The agent targeting RANK-L, e.g., anti-RANK-L antibody, e.g., denosumab, can be administered to the subject via any suitable route of administration. For example, the anti-RANK-L antibody (e.g., denosumab) can be administered to a subject via parenteral, nasal, oral, pulmonary, topical, vaginal, or rectal administration. In some embodiments, the anti-RANK-L antibody (e.g., denosumab) is administered to the subject by injection. In some embodiments, the anti-RANK-L antibody (e.g., denosumab) is administered to the subject by subcutaneous injection. In some embodiments, the anti-RANK-L antibody (e.g., denosumab) is administered to the subject by injection into the upper arm, upper thigh, or abdomen of the subject. In some embodiments, the anti-RANK-L antibody (e.g., denosumab) is administered to the subject by subcutaneous injection into the upper arm, upper thigh, or abdomen of the subject.

Similarly, the PD-1 inhibitor, e.g., nivolumab or pembrolizumab, can be administered to the subject via any suitable route of administration. For example, the PD-1 inhibitor (e.g., nivolumab or pembrolizumab) can be administered to a subject via parenteral, nasal, oral, pulmonary, topical, vaginal, or rectal administration. In some embodiments, the PD-1 inhibitor (e.g., nivolumab or pembrolizumab) is administered to the subject intravenously.

The following discussion on routes of administration is merely provided to illustrate non-limiting example embodiments and should not be construed as limiting the scope of the disclosure in any way.

Formulations suitable for parenteral administration include, but are not limited to, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term "parenteral" means not through the alimentary canal but by some other route such as subcutaneous, intramuscular, intraspinal, or intravenous. The anti-RANK-L antibody (e.g., denosumab) and/or the PD-1 inhibitor (e.g., nivolumab, pembrolizumab) can be administered with a physiologically acceptable diluent in a pharmaceutical carrier, such as a sterile liquid or mixture of liquids, including water, saline, aqueous dextrose and related sugar solutions, an alcohol, such as, e.g., ethanol or hexadecyl alcohol, a glycol, such as, e.g., propylene glycol or polyethylene glycol, dimethylsulfoxide, glycerol, ketals, such as, e.g., 2,2-dimethyl-153-dioxolane-4-methanol, ethers, poly (ethyleneglycol) 400, oils, fatty acids, fatty acid esters or glycerides, or acetylated fatty acid glycerides with or without the addition of a pharmaceutically acceptable surfactant, such as, e.g., a soap or a detergent, suspending agent, such as, e.g., pectin, carbomers, methylcellulose, hydroxypropylmethylcellulose, or carboxymethylcellulose, or emulsifying agents and other pharmaceutical adjuvants.

Oils which can be used in parenteral formulations include, but are not limited to, petroleum, animal, vegetable, and synthetic oils. Specific non-limiting examples of oils include peanut, soybean, sesame, cottonseed, corn, olive, petrolatum, and mineral. Suitable fatty acids for use in parenteral formulations include, but are not limited to, oleic acid, stearic acid, and isostearic acid. Ethyl oleate and isopropyl myristate are non-limiting examples of suitable fatty acid esters.

In some embodiments, the parenteral formulations contain from about 0.5% to about 25% by weight of the anti-RANK-L antibody (e.g., denosumab) in solution. Preservatives and buffers can be used. In order to minimize or eliminate irritation at the site of injection, such compositions can contain one or more nonionic surfactants having a hydrophile-lipophile balance (HLB) of from about 12 to about 17. In some embodiments, the quantity of surfactant in such formulations ranges from about 5% to about 15% by weight. Suitable surfactants include, but are not limited to, polyethylene glycol sorbitan fatty acid esters, such as, e.g., sorbitan monooleate and the high molecular weight adducts of ethylene oxide with a hydrophobic base, formed by the condensation of propylene oxide with propylene glycol. In some embodiments, the parenteral formulations are presented in unit-dose or multi-dose sealed containers, such as, e.g., ampoules and vials, and can be stored in a freeze-dried (lyophilized) condition requiring only the addition of the sterile liquid excipient, e.g., water, for injections, immediately prior to use. In some embodiments, extemporaneous injection solutions and suspensions are prepared from sterile powders, granules, and tablets.

Injectable formulations are in accordance with the present disclosure. The requirements for effective pharmaceutical carriers for injectable compositions are well-known to those of ordinary skill in the art (see, e.g., *Pharmaceutics and Pharmacy Practice*, J. B. Lippincott Company, Philadelphia, PA, Banker and Chalmers, eds., pages 238-250 (1982), and *ASHP Handbook on Injectable Drugs*, Toissel, 4th ed., pages 622-630 (1986)).

Safety

In some embodiments, the methods comprise administering an anti-RANK-L antibody (e.g., denosumab) in an amount that does not lead to a dose-limiting toxicity (DLT) during treatment with the anti-RANK-L antibody (e.g., denosumab). In some embodiments, the methods comprise administering a PD-1 inhibitor (e.g., nivolumab, pembrolizumab) in an amount that does not lead to a dose-limiting toxicity (DLT) during treatment with the PD-1 inhibitor (e.g., nivolumab, pembrolizumab). In some embodiments, the subject does not exhibit a DLT during the administration of the anti-RANK-L antibody (e.g., denosumab) and/or the PD-1 inhibitor (e.g., nivolumab, pembrolizumab). In some embodiments, the subject does not exhibit any grade 3 or grade 4 adverse events associated with treatment with the anti-RANK-L antibody (e.g., denosumab) and/or the PD-1 inhibitor (e.g., nivolumab or pembrolizumab) during the treatment period. In some embodiments, the subject does not exhibit any grade 3 or grade 4 adverse events associated with treatment with the anti-RANK-L antibody (e.g., denosumab) and/or the PD-1 inhibitor (e.g., nivolumab or pembrolizumab) during the treatment period. In some embodiments, the treatment period is at least one month (e.g., 2 months, 3, months, 4 months, 5 months, 6 months, 7 months, 8 months, 9 months, 10 months, 11 months, 12 months, 1 year). In some embodiments, the treatment period is at most one year.

In some embodiments, the subject is not hypocalcemic. In some embodiments, the subject is not hypocalcemic during the administration of the anti-RANK-L antibody (e.g., denosumab) and/or the PD-1 inhibitor (e.g., nivolumab, pembrolizumab). In some embodiments, the subject is not hypocalcemic prior to the administration of the anti-RANK-L antibody (e.g., denosumab) and/or the PD-1 inhibitor (e.g., nivolumab, pembrolizumab).

Administration Response

In some embodiments, a method disclosed herein is associated with an anti-tumor immune response and/or a tumor objective response. In some embodiments, a method disclosed herein is associated with an anti-tumor immune response. In some embodiments, a method disclosed herein is associated with a tumor objective response. In some embodiments, a method disclosed herein is associated with an anti-tumor immune response and a tumor objective response.

In some embodiments, a method disclosed herein is associated with an anti-tumor immune response within about three weeks of the administration of the first loading dose of denosumab. In some embodiments, a method disclosed herein is associated with an anti-tumor immune response within about 16 weeks of the administration of the first loading dose of denosumab.

In some embodiments, a method disclosed herein is associated with a tumor objective response within about 16 weeks of the administration of the first loading dose of denosumab. In some embodiments, a method disclosed herein is associated with a tumor objective response within about six months of the administration of the first loading dose of denosumab.

In some embodiments, the anti-tumor immune response is chosen from:

a change (e.g., an increase) in recent thymic emigrant cells (RTEs) in a peripheral blood sample from the subject relative to a baseline peripheral blood sample;

a change (e.g., an increase) in density of tumor-infiltrating cluster of differentiation (CD8+) cells (TILs) in a tumor tissue sample from the subject relative to a baseline tumor tissue sample;

an increase in the number of tumor-infiltrating CD8+ cells in a tumor tissue sample from the subject relative to a baseline tumor tissue sample as assessed by immunohistochemistry;

an increase in tumor cell death in a tumor tissue sample from the subject relative to a baseline tumor tissue sample as assessed by immunohistochemistry;

an increase in the total number of CD8+ and CD4+ non-Treg RTEs in a peripheral blood sample from the subject relative to a baseline peripheral blood sample as assessed by flow cytometric analysis;

an increase in the total number of CD4+ Treg cells in a peripheral blood sample from the subject relative to a baseline peripheral blood sample as assessed by flow cytometric analysis;

an increase in immune cell clonal diversity in a peripheral blood sample from the subject relative to a baseline peripheral blood sample as assessed by flow cytometric analysis;

an increase in the number of RANK+ Treg cells in a peripheral blood sample from the subject relative to a baseline peripheral blood sample as assessed by flow cytometric analysis;

at least partial suppression of myeloid-derived suppressor cells (MDSCs) in a peripheral blood sample from the subject relative to a baseline peripheral blood sample as assessed by flow cytometric analysis;

a decrease in the number of tumor-associated macrophages in a tumor tissue sample from the subject relative to a baseline tumor tissue sample; and a decrease in the number of tumor-infiltrating MDSCs in a tumor tissue sample from the subject relative to a baseline tumor tissue sample. Any one or more of these parameters is contemplated.

In some embodiments, the anti-tumor immune response is an increase in recent thymic emigrant cells (RTEs) in a peripheral blood sample from the subject relative to a baseline peripheral blood sample.

In some embodiments, the anti-tumor immune response is a change (e.g., an increase) in density of tumor-infiltrating cluster of differentiation (CD8+) cells (TILs) in a tumor tissue sample from the subject relative to a baseline tumor tissue sample.

In some embodiments, the anti-tumor immune response is an increase in the number of tumor-infiltrating CD8+ cells in a tumor tissue sample from the subject relative to a baseline tumor tissue sample as assessed by immunohistochemistry.

In some embodiments, the anti-tumor immune response is an increase in tumor cell death in a tumor tissue sample from the subject relative to a baseline tumor tissue sample as assessed by immunohistochemistry.

In some embodiments, the anti-tumor immune response is an increase in the total number of CD8+ and CD4+ non-Treg RTEs in a peripheral blood sample from the subject relative to a baseline peripheral blood sample as assessed by flow cytometric analysis.

In some embodiments, the anti-tumor immune response is an increase in the total number of CD4+ Treg cells in a peripheral blood sample from the subject relative to a baseline peripheral blood sample as assessed by flow cytometric analysis.

In some embodiments, the anti-tumor immune response is an increase in immune cell clonal diversity in a peripheral blood sample from the subject relative to a baseline peripheral blood sample as assessed by flow cytometric analysis.

In some embodiments, the anti-tumor immune response is an increase in the number of RANK+ Treg cells in a peripheral blood sample from the subject relative to a baseline peripheral blood sample as assessed by flow cytometric analysis.

In some embodiments, the anti-tumor immune response is at least partial suppression of myeloid-derived suppressor cells (MDSCs) in a peripheral blood sample from the subject relative to a baseline peripheral blood sample as assessed by flow cytometric analysis.

In some embodiments, the anti-tumor immune response is a decrease in the number of tumor-associated macrophages in a tumor tissue sample from the subject relative to a baseline tumor tissue sample.

In some embodiments, the anti-tumor immune response is a decrease in the number of tumor-infiltrating MDSCs in a tumor tissue sample from the subject relative to a baseline tumor tissue sample.

In some embodiments, the tumor objective response is a Complete Response or Partial Response as assessed using RECIST v1.1 criteria. In some embodiments, the tumor objective response is a Complete Response as assessed using RECIST v1.1 criteria. In some embodiments, the tumor objective response is a Partial Response as assessed using RECIST v1.1 criteria.

In some embodiments, a subject treated according to a method described herein does not experience a progression event or a death event within about one month of the administration of the first loading dose of denosumab. In some embodiments, a subject treated according to a method described herein does not experience a progression event or a death event within about two months of the administration of the first loading dose of denosumab. In some embodiments, a subject treated according to a method described herein does not experience a progression event or a death event within about three months of the administration of the first loading dose of denosumab. In some embodiments, a subject treated according to a method described herein does not experience a progression event or a death event within about four months of the administration of the first loading dose of denosumab. In some embodiments, a subject treated according to a method described herein does not experience a progression event or a death event within about five months of the administration of the first loading dose of denosumab. In some embodiments, a subject treated according to a method described herein does not experience a progression event or a death event within about six months of the administration of the first loading dose of denosumab. In some embodiments, a subject treated according to a method described herein does not experience a progression event or a death event within about seven months of the administration of the first loading dose of denosumab. In some embodiments, a subject treated according to a method described herein does not experience a progression event or a death event within about eight months of the administration of the first loading dose of denosumab. In some embodiments, a subject treated according to a method described herein does not experience a progression event or a death event within about nine months of the administration of the first loading dose of denosumab. In some embodiments, a subject treated according to a method described herein does not experience a progression event or a death event within about ten months of the administration of the first loading dose of denosumab. In some embodiments, a subject treated according to a method described herein does not experience a progression event or a death event within about eleven months of the administration of the first loading dose of denosumab. In some embodiments, a subject treated according to a method described herein does not experience a progression event or a death event within about one year of the administration of the first loading dose of denosumab.

The disclosed subject matter is not intended to be limited in scope by the specific embodiments described herein, which are instead intended as non-limiting illustrations of individual aspects of the disclosure. Functionally equivalent methods and components are within the scope of the disclosure. Indeed, various modifications of the disclosed subject matter, in addition to those shown and described herein, will be apparent to those skilled in the art from the foregoing description and accompanying drawing(s). Such modifications are intended to fall within the scope of the disclosed subject matter.

The descriptions of the various embodiments and/or examples of the disclosed subject matter have been presented for purposes of illustration, but are not intended to be exhaustive or limiting in any way. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, and/or to enable others of ordinary skill in the art to understand the disclosed subject matter.

EXAMPLES

In order that the present disclosure may be more fully understood, the following examples are set forth. It should with an anti-PD-1 agent (pembrolizumab or nivolumab) in patients with unresectable PD-1/PD-L1 inhibitor-naïve regional and distant metastatic melanoma (AJCC stage III/IV). Patients must have available baseline tumor tissue and undergo a day 22 (mandatory) and week 15 (optional) research biopsy to participate. Pharmacodynamic and antitumor effects are investigated by performing translational research on peripheral blood and tumor tissue collected before and during denosumab treatment alone and in combination with anti-PD-1 treatment.

Up to 25 subjects have received denosumab at an FDA-approved dose (120 mg subcutaneously (s.c.) every 4 weeks, administered in the upper arm, upper thigh, or abdomen), with additional loading doses of denosumab 120 mg s.c. on day 8 and day 22 (FIG. 1). Nivolumab, 480 mg, was administered intravenously (IV) every 4 weeks and initiated 21 days after the first dose of denosumab was given. In subjects enrolled prior to Amendment 1, pembrolizumab, 200 mg was administered intravenously (IV) every 3 weeks and initiated 21 days after the first dose of denosumab is given. On days when denosumab is administered on the same day as an anti-PD-1 agent (e.g., 21 days after the first dose of denosumab is administered), the s.c. injection should be given after the infusion of the anti-PD-1 agent is completed. Combination therapy with both agents continue as long as subjects benefit from therapy, for up to 1 year. Study therapy is discontinued for intolerable toxicity, disease progression, or for other reasons at the discretion of the investigator. If subjects are not withdrawn prematurely, then their last dose of study medications will be administered approximately 49 weeks after denosumab was initiated.

TABLE 5

| Treatment Dosage and Administration | | | | |
|---|---|---|---|---|
| Agent | Required Premedications; Precautions | Dose | Route | Schedule |
| Denosumab | Correct hypocalcemia prior to initiating denosumab therapy. Monitor calcium levels during therapy, especially during the first 8 weeks of therapy, and adequately supplement all subjects with calcium ($\geq$500 mg qd) and vitamin D ($\geq$400 IU qd). Monitor calcium, magnesium and phosphorus. | 120 mg | s.c.; Administer in upper arm, upper thigh or abdomen | Every 28 days. Additional loading doses of 120 mg s.c. administered on days 8 and 22 |
| Nivolumab | Risk for immune-mediated and, infusion-related reactions | 480 mg | IV; Administer over 30 min | Every 28 days |
| Pembrolizumab | Risk for immune-mediated and infusion-related reactions | 200 mg | IV; Administer over 30 min | Every 21 days | be understood that these examples are for illustrative purposes only and are not to be construed as limiting this disclosure in any manner.

Example 1: Phase 2 Study of Denosumab in Combination with a PD-1 Inhibitor in Subjects with Stage III/IV Melanoma An ongoing multicenter open-label, single-arm, phase II study (ClinicalTrials.gov Identifier: NCT03620019) was designed to investigate the pharmacodynamic (PD) and antitumor effects of denosumab alone and in combination The Phase 2 study has co-primary objectives; one being to assess the pharmacodynamic effects (immunomodulatory and/or antitumor) of denosumab alone and the other being to assess the pharmacodynamic effects following combination therapy with denosumab and an anti-PD-1 agent. To investigate any potential direct antitumor and indirect immunomodulatory effects of denosumab alone, concomitant anti-PD-1 treatments do not start until day 22 of study treatment initiation. Optional tumor tissue is collected from any procedures that took place prior to study enrollment. Mandatory tumor biopsies and peripheral blood are collected on day 22, immediately prior to the first anti-PD-1 agent infusion.

Peripheral blood samples are collected at weeks 16, 28, and 40. Optional tumor tissue also is collected at the end of week 16 and on any procedures that occur after study completion or study removal due to tumor progression.

Excised tumors are fixed in formalin and paraffin-embedded (FFPE). Hematoxylin and eosin (H&E)-stained tissue sections will be generated to assess the quality (necrosis) and amount of tumor cells present. In addition, the amount of TILs are scored, as previously described (Cancer Genome Atlas N: Genomic Classification of Cutaneous Melanoma. Cell 161:1681-96, 2015). Furthermore, 5-μm thick tissue sections will be prepared to perform tumor-imaging analysis (e.g., CD8, RIP3, Apoptag®, Sox10, RANK, RANKL, OPG, PD-1, CD68, CD163, CD33, CD11b, HLA-DR).

Serum levels of RANKL (free and OPG-bound) and OPG in peripheral blood samples are measured by ELISA. Additionally, the following peripheral blood mononuclear cell populations will be enumerated using multiparameter flow cytometry:

Bone marrow-derived double negative early thymocytes (baseline, week 4, week 16, 28, and 40) CD34+CD2+CD4-CD5+CD7+CD8-CD45RA+;

RTE by flow cytometric analysis (baseline, week 4, week 16, 28, and 40) CD4+CD45RO-CD45RA+CD62L+CD31+, CD4+Foxp3+CD45RO-CD45RA+CD62L+CD31+, and CD8+CD45RO-CD45RA+CD62L+CD31+;

RTE by sjTREC analysis on FACS-sorted CD4+ and CD8+ PBMCs (baseline, week 4, week 16, 28, and 40);

Immune cell receptor repertoire analysis on FACS-sorted CD4+ and CD8+ PBMCs (baseline, week 4, week 16, 28, and 40);

Effector T cell subtypes (baseline, week 4, week 16, 28, and 40), such as cytotoxic (CD3+CD4-CD8+Granzyme B+) and exhausted (CD3+CD4-CD8+PD-1+TIM3+LAG3+);

Treg cells (baseline, week 4, week 16, 28, and 40) CD4+CD25high+FoxP3+(RANKL);

MDSC (baseline, week 4, week 16, 28, and 40; Su's lab) monocytic (HLA-DRlowCD14+), other monocytic (lin1⁻HLA-DR⁻CD33+CD11b+), lymphoid (lin1⁻HLA-DR⁻CD33+CD11b+).

The secondary co-primary endpoint of the study includes assessment of the pharmacodynamic effects of denosumab and anti-PD-1 agent combination therapy in peripheral blood samples collected during the study (i.e., at weeks 16, 28, and 40) for comparison with denosumab alone. An optional tumor biopsy may be obtained at week 16. Secondary endpoints include assessments to determine the safety of the combination in subjects with metastatic melanoma, plus measurements of the clinical benefit of denosumab in combination with an anti-PD-1 agent based on response rate, per Response Evaluation Criteria in Solid Tumors version 1.1 (RECIST v1.1) criteria at week 16, progression-free survival (PFS) rate at 6 months of combination therapy, and overall survival (OS) rate at 1-year of study treatment. The safety of the combination is evaluated per NCI Common Terminology Criteria for Adverse Events (NCI-CTCAE). Pre-defined Pocock-stopping criteria will dictate early trial termination, if excessive toxicity or other adverse effects (AE) of clinical interest are observed with this combination.

Inclusion criteria for the Phase 2 study include:

1. Signed written informed consent and HIPAA authorization for release of personal health information.

2. Age ≥18 years at the time of consent.

3. Eastern Cooperative Oncology Group (ECOG) Performance Status of 0-2.

4. Histologically confirmed melanoma of cutaneous or mucosal primary; (e.g. sinus, vagina, anus, gastrointestinal tract); metastatic melanomas from unknown primary are allowed because melanoma of unknown primary is biologically similar to cutaneous melanomas.

5. AJCC stage III/IV unresectable (or resectable) disease. Both should be measurable by RECIST v1.1 criteria. Patients with resectable bulky stage IIIB, state IIIC or stage IIID melanoma (≥2-cm in shortest diameter for lymph nodes infiltrated by tumor and ≥2-cm in longest diameter for non-lymph nodes infiltrated by tumor) can also be entered into the study at the discretion of the Principal Investigator.

6. Must have available and consent to collect archived tumor blocks from previous surgeries confirming or treating metastatic disease (e.g. radical lymph node dissection); if not available or of insufficient quantity (e.g. <2-mm2 size tumor) or quality (>50% necrosis, <30% tumor cells) they can be enrolled into the trial, if they consent to have a tumor biopsy before treatment initiation.

7. Must agree to undergo one on-treatment biopsy on week 4 of the study; the biopsy at week 16 is optional.

8. Must agree to have 100 mL blood drawn for study purposes on week 1, day 20+ or −2 (week 4), week 16, week 28, week 40 and end of treatment.

9. Demonstrate adequate organ function, as defined in the table; all screening labs to be obtained within 21 days prior to registration.

10. Females of childbearing potential must have a negative serum pregnancy test within 72 hours prior to study treatment. Note: Females are considered of child bearing potential unless they are surgically sterile (have undergone a hysterectomy, bilateral tubal ligation, or bilateral oophorectomy) or they are naturally postmenopausal for at least 12 consecutive months.

11. Females of childbearing potential must be willing to use adequate method of contraception—Oral contraception is required 14 days prior to initiation of study medications until 120 days after treatment discontinuation. Note: Abstinence is acceptable if this is the usual lifestyle and preferred contraception for the subject.

12. Male patients with female partners must have had a prior vasectomy or agree to use an adequate method of contraception—Contraception, starting with the first dose of study therapy through 120 days after the last dose of study therapy. Note: Abstinence is acceptable if this is the usual lifestyle and preferred contraception for the subject.

13. As determined by the enrolling physician or protocol designee, willingness and ability of the subject to understand and comply with study procedures.

14. Previous radiation therapy is allowed, provided it is completed ≥14 days prior to starting denosumab and patient has recovered adequately from any related toxicities (grade ≤1, or grade ≤2 that is stable for ≥3 months).

15. If patient has received adjuvant treatments, in particular ipilimumab and high dose interferon, any toxicities must have resolved to grade 1 or less. Grade 2 toxicities attributed to ipilimumab from autoimmune endocrinopathies that require permanent hormone replacement therapy are allowed as long as they are adequately treated. This implies that patients should be off systemic steroids for treatment of any of these or other autoimmune toxicities (e.g. colitis, rash).

Additionally, subjects who have previously received PD-1 inhibitors in stage III (adjuvant) or stage IV may enroll in the Phase 2 study as long as:

1. the interval between the last dose of the adjuvant PD-1 inhibitor and the date of relapse (clinical or radiographic) is at least 1 year, 2. if subjects who received treatment for stage IV had antitumor response (partial response or complete response) by RECIST criteria version 1.1 but they stopped due to subject/investigator preference for at least a year between the last dose of the PD-1 inhibitor and the date of relapse (clinical or radiographic). Allowing for these subjects who have previously received PD-1 inhibitors in the adjuvant setting (i.e. no knowledge about clinical benefit) or following definite antitumor response in the metastatic setting is based on a recent case series of subjects who responded to PD-1 inhibitor rechallenge, if they had previously responded to PD-1 inhibitors. This implies that waning antitumor immunity in the absence (i.e. >1 year) of costimulation with PD-1 inhibitors may be the reason for cancer recurrence and NOT primary resistance of PD-1 inhibitors.

3. any side effects that may have occurred during the previous exposure to PD-1 inhibitors are not serious (i.e. grade 1 or 2 by CTCAE version 5.0 criteria).

Exclusion criteria for the Phase 2 study include:

1. History of prior malignancy, with the exception of the following:

Non-melanoma skin cancers, non-invasive bladder cancer, and carcinoma in situ of the cervix, Prior history of prostate, provided that patient is not under active systemic treatment other than hormonal therapy and with documented undetectable prostate specific antigen (PSA <0.2 ng/ml), Chronic lymphocytic leukemia (CLL)/small lymphocytic lymphoma (SLL) provided patient has isolated lymphocytosis (Rai stage O), and does not require systemic treatment [for "B" symptoms, Richter's transformation, lymphocyte doubling time (<6 months), lymphadenopathy or hepatosplenomegaly], Lymphoma or any type or hairy-cell leukemia, provided patient is not on an active systemic treatment and is in complete remission, as evidenced by Positron Emission Tomography (PET)/CT scans and bone marrow biopsies for at least 3 months, History of other malignancy, provided patient has completed therapy, or does not require therapy, and is free of disease for ≥2 years. If patient has had other malignancy within the last 2 years from which he/she may have been completely cured by surgery alone, or does not require any treatment other than observation at the specialist's discretion, he/she may be considered to be enrolled on condition that the risk of development of recurrent or distant metastatic disease based on the American Joint Committee in Cancer (AJCC) staging system is less than 30% in 3 years from the original diagnosis of other malignancy.

2. Has known active central nervous system (CNS) metastases that are symptomatic and require antiepileptic drugs or corticosteroids. Subjects with previously treated brain metastases may participate provided they are stable (without evidence of progression by imaging) for at least 2 weeks prior to the first dose of trial treatment and any neurologic symptoms have returned to baseline, have no evidence of new or enlarging brain metastases, and are not using steroids for at least 7 days prior to trial treatment. This exception does not include carcinomatous meningitis, which is excluded regardless of clinical stability. Patients with leptomeningeal disease, detected either by brain MRI or by cytology (e.g. lumbar puncture) or also excluded.

3. Treatment with any investigational drug, immunotherapy or chemotherapy within 28 days prior to study treatment (i.e., initiation of denosumab). Treatment with any targeted therapy (e.g. Mitogen-Activated Protein Kinases (MAPK) inhibitors) is allowed as long as at least 15 days have elapsed since last dose of drug.

4. Patients discontinuing prior therapy with tyrosine kinase inhibitors for melanoma should be off these medications for at least 15 days before starting study treatment.

5. Prior PD-1/PD-L1 therapies in the adjuvant setting; targeted therapies or prior ipilimumab in the adjuvant setting are allowed.

6. Any condition, including laboratory abnormalities, that in the opinion of the investigator places the subject at unacceptable risk, if he/she were to participate in the study. This includes, but is not limited, to serious medical conditions or psychiatric illness likely to interfere with participation in this clinical study.

7. Has a diagnosis of immunodeficiency or is receiving systemic steroid therapy equivalent to daily doses of prednisone of 10 mg or greater (or an equivalent dose of other corticosteroids) or any other form of immunosuppressive therapy within 7 days prior to the first dose of trial treatment.

8. Has a known history of active tuberculosis (Mycobacterium Bacillus Tuberculosis).

9. Is pregnant or breastfeeding, or expecting to conceive or father children within the projected duration of the trial, starting with the pre-screening or screening visit through 120 days after the last dose of trial treatment.

10. Hypersensitivity to nivolumab, pembrolizumab or denosumab or any of their excipients.

11. Has active autoimmune disease that has required systemic treatment in the past 2 years (i.e. with use of disease-modifying agents, corticosteroids or immunosuppressive drugs). Replacement therapy (e.g., thyroxine, insulin, or physiologic corticosteroid replacement therapy for adrenal or pituitary insufficiency, etc.) is not considered a form of systemic treatment.

12. Has a history of non-infectious pneumonitis that required systemic corticosteroids or evidence of interstitial lung disease or current active, non-infectious pneumonitis. Episodic, brief (<7 day) exposure to systemic corticosteroids (e.g. steroid taper for poison ivy or Chronic Obstructive Pulmonary Disease (COPD) exacerbation) is allowed.

13. Has a history of an acute coronary event (e.g. myocardial infarction) within 3 months since study entry, uncontrolled and symptomatic coronary artery disease, or congestive heart failure New York Heart Association class III/IV.

14. Has an active infection requiring systemic therapy within 7 days prior to treatment initiation.

15. Has a known history of Human Immunodeficiency Virus (HIV ½ antibodies).

16. Known serologic status reflecting active hepatitis B or C infection. Patients that are hepatitis B core antibody positive, but antigen negative, will need a negative polymerase chain reaction (PCR) prior to enrollment. [Note: Hepatitis B antigen or PCR positive patients will be excluded].

17. Has received a live vaccine within 30 days of planned start of study therapy. Note: Seasonal influenza vaccines for injection are generally inactivated flu vaccines and are allowed; however intranasal influenza vaccines (e.g., Flu-Mist®) are live attenuated vaccines, and are not allowed.

18. Known active metabolic bone disease such as Paget's disease, Cushing's disease, hyperprolactinemia, over the last year 12 months, known history of osteoporosis that is symptomatic (e.g. history of fractures, bone pain), or hypercalcemia/hypocalcemia of any type (serum free calcium being more than 1.1×upper limit of normal (ULN) and less than 0.9×, lower limits normal. LLN) over the last 2 weeks since study initiation that requires treatment beyond calcium and vitamin D supplementation.

19. Prior treatment with denosumab. Use of bisphosphonates for treatment of metastatic bone disease, but not for hypercalcemia of malignancy, is allowed.

20. History of current evidence of osteonecrosis or osteomyelitis of the jaw, active dental or jaw problems necessitating known invasive dental procedure during the study, or non-healed dental or oral surgery. Note: Patient should be referred to dentist before study treatment initiation for poor dentition or other dental issues that, in the opinion of the treating physician, may increase the risk of osteonecrosis of the jaw.

22 patients treated with denosumab and nivolumab were evaluable (median age, 60 years old; 12 males; 19 cutaneous; 5 stage IIIB-C; 3 with bone metastases). Immune-mediated fatigue and arthralgias attributed to denosumab alone (first 3 weeks) were seen in ten and four patients, respectively. Six patients developed tumor pain during denosumab±nivolumab treatment. Additionally, one subject developed colitis, and another developed pneumonitis; these adverse events (AEs) were attributed to nivolumab, which was permanently discontinued. Each of the two patients re-developed grade 2 pneumonitis and colitis upon rechallenge with denosumab alone. Response rate (RR) (partial response (PR)+complete response (CR)) was 50%. Two patients had antitumor responses before nivolumab initiation; both patients had brisk (3+) TILs at their baseline tumor.

At a median follow-up of 19.9 months (range, 5-44.1 months), the median PFS was 13.3 months (range, 1.1 to 41.4+ months). Eleven patients had not progressed. Five patients had died, including four from metastatic melanoma (one from COVID-19 complications).

At a median follow-up of 21.8 months, five patients had died from melanoma and one patient had died from complication from COVID-19 infection; the latter patient had achieved complete radiographic response. Seven patients are currently alive with no evidence of melanoma.

The median progression-free survival of the denosumab-nivolumab combination is 14.9 months (range 1.1 months, 57.4+ months). The median progression-free survival of the most recently published trial of nivolumab plus relatlimab (Tawbi et al., N Engl J Med 386: 24-24, 2022) was 10.1 months. This suggests that the nivolumab-denosumab combination is active in metastatic melanoma. The median overall survival of the denosumab-nivolumab combination was 21.8 months (range 4.4 months, 57.4+ months).

Based on the patients evaluated to date, denosumab alone has infrequent antitumor activity and induces mild immune-mediated AEs. Denosumab in combination with a PD-1 inhibitor, e.g., nivolumab, appears to be well-tolerated and appears to have higher RR than prior studies with single-agent PD-1 inhibitor.

---

What is claimed is:

1. A method of treating melanoma in a subject in need thereof, comprising administering to said subject: (1) 120 mg denosumab via subcutaneous administration; and (2) 480 mg nivolumab or 200 mg pembrolizumab via intravenous administration, wherein the subject does not have bone metastases, and wherein:

said denosumab comprises a heavy chain comprising the amino acid sequence of SEQ ID NO:11, and light chain comprising the amino acid sequence of SEQ NO: 12;

said nivolumab comprises a heavy chain comprising the amino acid sequence of SEQ ID NO:21, and light chain comprising the amino acid sequence of SEQ NO: 22; and said pembrolizumab comprises a heavy chain comprising the amino acid sequence of SEQ ID NO:31, and light chain comprising the amino acid sequence of SEQ NO: 32.

2. The method of claim 1, wherein denosumab is administered once every 4 weeks (Q4W), with one or more additional loading doses administered between Day 2 and Day 22.

3. The method of claim 1, wherein three doses of denosumab are administered between Day 1 to Day 22, inclusive.

4. The method of claim 1, wherein denosumab is administered on Day 1, Day 8, and Day 22, and subsequently once every 4 weeks (Q4W) after Day 22.

5. The method of claim 1, wherein one or more doses of denosumab are administered prior to the administration of the first dose of nivolumab or pembrolizumab.

6. The method of claim 1, wherein one or more doses of denosumab are administered between Day 1 to Day 22, inclusive, and subsequently once every 4 weeks (Q4W) from Day 22; and wherein nivolumab is administered once every 4 weeks (Q4W) from Day 22.

7. The method of claim 1, wherein three doses of denosumab are administered between Day 1 to Day 22, inclusive, and subsequently once every 4 weeks (Q4W) from Day 22; and wherein nivolumab is administered once every 4 weeks (Q4) from Day 22.

8. The method of claim 1, wherein three doses of denosumab are administered at Day 1, Day 8, and Day 22, inclusive, and subsequently once every 4 weeks (Q4W) from Day 22; and wherein nivolumab is administered once every 4 weeks (Q4W) from Day 22.

9. The method of claim 1, wherein one or more doses of denosumab are administered between Day 1 to Day 22, inclusive, and subsequently once every 4 weeks (Q4W) from Day 22; and wherein pembrolizumab is administered once every 3 weeks (Q3W) from Day 22.

10. The method of claim 1, wherein three doses of denosumab are administered between Day 1 to Day 22, inclusive, and subsequently once every 4 weeks (Q4W) from Day 22; and wherein pembrolizumab is administered once every 3 weeks (Q3W) from Day 22.

11. The method of claim 1, wherein three doses of denosumab are administered at Day 1, Day 8, and Day 22, and subsequently once every 4 weeks (Q4W) after Day 22; and wherein pembrolizumab is administered once every 3 weeks (Q3W) from Day 22.

12. The method of claim 1, wherein the subject previously received a PD-1 inhibitor treatment.

13. The method of claim 1, wherein the subject is not co-administered with an anti CTLA4 agent.

14. The method of claim 1, wherein the subject is not co-administered with ipilimumab.

15. The method of claim 1, wherein the melanoma is stage III melanoma or stage IV melanoma.

16. The method of claim 1, wherein the melanoma is cutaneous melanoma or mucosal melanoma.

17. The method of claim 1, wherein the melanoma is unresectable.

18. The method of claim 1, wherein the subject previously received a PD-1 inhibitor treatment, and the interval between the last dose of the previously received PD-1 inhibitor treatment and the date of relapse is at least one year.

* * * * *